(12) United States Patent
Pargass et al.

(10) Patent No.: US 6,645,330 B2
(45) Date of Patent: Nov. 11, 2003

(54) METHOD OF MAKING DISPOSABLE ABSORBENT ARTICLE HAVING GRAPHICS USING ULTRASONIC THERMAL IMAGING

(75) Inventors: Sunita Pargass, Norcross, GA (US); Joseph Vergona, Suwanee, GA (US)

(73) Assignee: Paragon Trade Brands, Inc., Norcross, GA (US)

( * ) Notice: Subject to any disclaimer, the term of this patent is extended or adjusted under 35 U.S.C. 154(b) by 0 days.

(21) Appl. No.: 10/033,901

(22) Filed: Jan. 3, 2002

(65) Prior Publication Data

US 2003/0121588 A1 Jul. 3, 2003

(51) Int. Cl.[7] .................................................. B32B 31/16
(52) U.S. Cl. ........................ 156/73.1; 156/209; 156/359; 156/580.2
(58) Field of Search ..................... 156/64, 73.1, 250, 156/256, 269, 196, 199, 209, 359, 517, 521, 555, 580.1, 580.2, 582

(56) References Cited

U.S. PATENT DOCUMENTS

| | | |
|---|---|---|
| 3,113,225 A | 12/1963 | Kleesattel et al. |
| 3,562,041 A | 2/1971 | Robertson |
| 3,733,238 A | 5/1973 | Long et al. |
| 3,911,187 A | 10/1975 | Raley |
| 4,323,068 A | 4/1982 | Aziz |
| 4,518,643 A | 5/1985 | Francis |
| 4,592,943 A | 6/1986 | Cancian et al. |
| 4,646,362 A | 3/1987 | Heran et al. |
| 4,668,316 A | 5/1987 | Sager |
| 4,774,124 A | 9/1988 | Shimalla et al. |
| 5,096,532 A | 3/1992 | Neuwirth et al. |
| 5,110,403 A | 5/1992 | Ehlert |
| 5,229,186 A | 7/1993 | Tribble et al. |
| 5,235,515 A | 8/1993 | Ungpiyakul et al. |
| 5,248,543 A | 9/1993 | Yamaguchi et al. |
| 5,281,207 A | 1/1994 | Chmielewski et al. |
| 5,286,543 A | 2/1994 | Ungpiyakul et al. |
| 5,503,076 A | 4/1996 | Yeo |
| 5,599,420 A | 2/1997 | Yeo et al. |
| 5,612,118 A | 3/1997 | Schleinz et al. |
| 5,614,283 A | 3/1997 | Potnis et al. |
| 5,635,275 A | 6/1997 | Biagioli et al. |
| 5,716,477 A | 2/1998 | Yamaguchi et al. |
| 5,766,389 A | 6/1998 | Brandon et al. |
| 5,846,377 A | 12/1998 | Frantz et al. |
| 5,863,288 A | 1/1999 | Baker |
| 5,897,541 A | 4/1999 | Uitenbroek et al. |
| 6,036,796 A | 3/2000 | Halbert et al. |
| 6,041,701 A | 3/2000 | Louis Dit Picard et al. |
| 6,075,178 A | 6/2000 | La Wilhelm et al. |
| 6,117,562 A | 9/2000 | Yamaguchi et al. |
| 6,165,298 A | 12/2000 | Samida et al. |
| 6,165,306 A | 12/2000 | Rajala |
| 6,203,636 B1 | 3/2001 | Popper et al. |
| 6,277,224 B1 | 8/2001 | Muesch et al. |
| 6,297,424 B1 | 10/2001 | Olson et al. |
| 6,307,119 B1 | 10/2001 | Cammarota et al. |

*Primary Examiner*—James Sells
(74) *Attorney, Agent, or Firm*—Hunton & Williams

(57) ABSTRACT

An absorbent article including one or more images disposed thereon and a method for making the same are provided according to the present invention, wherein an ultrasonic assembly is used to impart sufficient energy to a deformed web to either partially or fully melt the web either in the deformed areas, or non-deformed areas to thereby form an image. The method can be used to print graphics directly on an absorbent article after its formation, or it can be used to print graphics on an appliqué layer that is subsequently placed on a predetermined portion of the absorbent article.

74 Claims, 8 Drawing Sheets

METHOD OF MAKING DISPOSABLE ABSORBENT ARTICLE HAVING GRAPHICS USING ULTRASONIC THERMAL IMAGING

BACKGROUND OF THE INVENTION

1. Field of the Invention

The present invention relates to disposable absorbent articles, and more particularly to disposable absorbent articles having graphics thereon. The invention also relates to processes and apparatus for making absorbent articles having graphics thereon whereby the graphics are made using ultrasonic thermal imaging methods.

2. Description of Related Art

Absorbent articles, and in particular disposable absorbent articles such as infant diapers or training pants, adult incontinence products and other such products, typically are constructed with a moisture-impervious outer backing sheet (or "backsheet"), a moisture-pervious body-contacting inner liner sheet (or "topsheet"), and a moisture-absorbent core (or "absorbent core") sandwiched between the liner sheet and the backing sheets. These disposable absorbent articles oftentimes include additional features such as elastic waist bands, elastic leg bands, and stretchable side panels. Further, decorative graphics can be incorporated into the disposable absorbent article for aesthetic and functional purposes.

Disposable absorbent articles generally are assembled on an automated production line by separately supplying the individual components of the absorbent article to the production line at predetermined locations along the machine direction, and layering the individual components to form an integrated absorbent article. Various methods are available for bringing these individual components together so that the components in the integrated product are in a desired relation with respect to each other. In bringing these individual components together, various known methods have been used to sense the position of a particular component, and then to adjust the placement of subsequent components in order to properly position them with respect to the previously sensed component. Proper placement of the components is even more important when one or more component(s) have graphics or other identifying marks printed or embossed thereon.

U.S. Pat. Nos. 5,286,543 and 5,235,515 to Ungpiyakul et al. disclose a system for selectively providing predetermined segments of web material that have printed graphics to an absorbent article production line using a reference marker that is incorporated into the final assembled absorbent article. Generally stated, the method includes supplying the web material at a web speed and sensing a reference mark on the web material to generate at least one reference mark datum which is associated with a selected web segment. The '543 Patent discloses that the predetermined segments of web material comprise discrete graphic patches corresponding to the tape landing zone of the diaper. The patch is said to have a predetermined set of graphics which are "congruously entire." The patches are also said to abruptly change from graphics set to graphics set and, therefore, from diaper to diaper because there is no modulating transition between the adjacent compositions formed on the original supply roll of web material. The patches are said to be provided with reference markers delineating the boundaries between individual web or patch segments. The reference markers comprise any signaling mechanism which is recognizable by a machine.

U.S. Pat. No. 5,766,389 to Brandon et al. discloses a process for controllably registering a plurality of components of a continuously moving first layer with a plurality of reference marks on a continuously moving second layer with pre-printed graphics. Brandon is said to controllably register a graphic within a designated area of the absorbent article. The '543 patent and Brandon both require transfer of a graphic from one supply of web material to the absorbent garment by cutting and placing the supply of web material including the graphic(s) on the absorbent garment.

Embossed plastic films are known in the art and are used as a substitute for textiles. Embossed films may be used for many different purposes such as diaper liners, panty liners and sanitary napkins. Examples of embossed films are disclosed in U.S. Pat. Nos. 3,911,187, 4,518,643, and 5,229,186, the disclosures of each of which are incorporated by reference herein in their entirety, and in a manner consistent with this disclosure. Embossing typically is used to alter the "feel" or "hand" of the fabric, and to add a decorative design. Different methods for embossing non-woven fabrics and films are known, some of which are designed primarily to alter the strength properties of the fabric, as disclosed in U.S. Pat. No. 4,592,943, the disclosure of which is incorporated by reference herein in its entirety. The '943 patent discloses heating a non-woven web as it passes between two grids so that the grids impart a pattern of rectangular densified areas to the web. Another method referred to as pattern roll embossing is disclosed in U.S. Pat. No. 4,774,124, the disclosure of which is incorporated by reference herein in its entirety, which discloses using a pair of pattern rollers to emboss non-woven fabric. Patterned and embossed non-woven materials also are described in U.S. Pat. No. 5,599,420, the disclosure of which is incorporated by reference herein in its entirety, and in a manner consistent with this disclosure. The '420 patent discloses a non-woven fabric comprising continuous polymeric filaments extending continuously along the length of the fabric that are bonded together with a heat-activated adhesive. Upon embossing, the fabric is said to have a pattern of densified areas separated by high loft areas.

Thermoplastic films have been bonded to one another with ultrasonic energy using embossed patterns or pins. Ultrasonic bonding and embossing techniques are disclosed in, for example, U.S. Pat. No. 3,562,041 (ultrasonic joining of materials according to a pattern), U.S. Pat. No. 3,733,238 (vibration welding of sheet materials), U.S. Pat. No. 4,668,316 (welding thin thermoplastic film by ultrasonic energy), U.S. Pat. No. 5,096,532 (ultrasonic rotary horn), U.S. Pat. No. 5,110,403 (high efficiency ultrasonic rotary horn), U.S. Pat. No. 5,846,377 (welding thermoplastic work pieces using ultrasonic energy), U.S. Pat. No. 6,036,796 (ultrasonic welding apparatus and method), U.S. Pat. No. 6,165,298 (patterned anvil roll to effect bonding, cutting, embossing, perforating), and U.S. Pat. No. 6,277,224 (ultrasonic perforator), the disclosures of each of which are incorporated by reference herein in their entirety. It also is known to use heated rolls to thermally emboss a web of material, as disclosed, for example, in U.S. Pat. Nos. 5,229,186 and 6,041,701, the disclosures of each of which are incorporated by reference herein in their entirety.

It also is common to use inks, e.g., adhesive inks, to form an image on a non-woven fabric. U.S. Pat. No. 5,503,076, the disclosures of which is incorporated by reference herein in its entirety, and in a manner consistent with this disclosure, discloses laminating a non-woven web facing layer and a substrate layer with colored adhesive inks that are applied in a discrete bond pattern. Thermal imaging techniques useful in forming images on various substrates are disclosed in, for example, U.S. Pat. Nos. 5,716,477 and 6,117,562, the disclosures of each of which are incorporated by reference herein in their entirety, and in a manner consistent with this disclosure.

SUMMARY OF THE INVENTION

It would be desirable to provide an absorbent garment having a graphic formed thereon, whereby the image can be formed on the backsheet or outer liner in-line during manufacture of the article. It also would be desirable to provide a method of forming a viewable image on an absorbent article that is cost efficient and easy to carry out. It would further be desirable to provide a method of forming an image on a moving web of material that is efficient, can operate at high line speeds, does not damage the moving web when the system shuts down, and that enables a more precise application of heat.

Accordingly, it is a feature of an embodiment of the invention to provide an absorbent garment and a method of making the absorbent garment whereby a viewable image is formed directly on the garment as it is manufactured in a cost-efficient manner. It is another feature of an embodiment of the invention to provide an efficient method of forming an image on a moving web at high speeds without causing significant damage and/or deformation of the moving web. It also is a feature of an embodiment of the invention to form an image on a moving web in a cost-efficient manner without causing significant damage and/or deformation to the moving web, and then transfer the image to a component in an absorbent garment.

In accordance with these and other features of various embodiments of the invention, there is provided a method of making an absorbent article, wherein each absorbent article comprises an image either formed on a moving web that forms a part of the article, or on an applique layer that then is subsequently adhered to or otherwise associated with the absorbent article. The method includes imparting sufficient ultrasonic energy with an ultrasonic assembly to the moving web or applique layer to raise the surface temperature of the moving web only in the areas where the image is to be formed to slightly above the melting temperature of the moving web or applique layer, and thereby form the image. In accordance with the method, the ultrasonic horn vibrates transversely to the direction of the moving web or applique layer, and preferably only briefly comes into contact with the material that is imaged when the horn is fully extended (e.g., at its greatest amplitude of vibration). It is particularly preferred in the invention that the amount of energy imparted by the ultrasonic horn be controlled to prevent forming a hole in the web or applique layer that can be caused by melting all the way through the material.

The method according to another embodiment of the invention is a method of forming an absorbent article that includes providing an absorbent core, and a top sheet material. The method also includes forming an image on a moving liquid impermeable back sheet material by imparting sufficient ultrasonic energy with an ultrasonic assembly to the back sheet material to raise the surface temperature thereof only in the areas where the image is to be formed to slightly above the melting temperature of the back sheet layer to thereby form a liquid impermeable imaged back sheet material. The method includes providing a liquid impermeable imaged back sheet material, and forming an absorbent article at a forming station by disposing the absorbent core between the top sheet material and the liquid impermeable imaged back sheet material.

In accordance with another feature of an embodiment of the invention, there is provided a method of making an absorbent article comprising supplying an absorbent core, a top sheet material and a liquid impermeable back sheet material. The method also includes forming an image on a moving applique layer by imparting sufficient ultrasonic energy with an ultrasonic assembly to the applique layer to raise the surface temperature thereof only in the areas where the image is to be formed to slightly above the melting temperature of the applique layer to form an imaged applique layer. The method further includes forming a continuously moving absorbent core assembly at a forming station by disposing the absorbent core between the top sheet material and the liquid impermeable back sheet material. In accordance with this embodiment, the method also includes providing a continuously moving imaged applique layer, and disposing the continuously moving imaged applique layer on a surface of the continuously moving absorbent core assembly.

In accordance with another feature of an embodiment of the invention, there is provide a method of imparting an image to an absorbent article that includes providing an absorbent core, a top sheet material, and a liquid impermeable back sheet material. The method further includes forming a continuously moving absorbent core assembly having at least one outer layer at a forming station by disposing the absorbent core between the top sheet material and the liquid impermeable back sheet material. The method also includes forming an image on the continuously moving absorbent core assembly by imparting sufficient ultrasonic energy with an ultrasonic assembly to the at least one outer layer to raise the surface temperature thereof only in the areas where the image is to be formed to slightly above the melting temperature of the outer layer.

In accordance with yet another embodiment of the invention, there is provided an apparatus for imparting an image to a moving non-woven web, the apparatus including a mechanism for transporting the web in a machine direction and past an ultrasonic assembly, an imaging roll capable of deforming the surface of the web without punching holes there through, whereby the deformed surface corresponds to either a positive or a negative of the image to be formed. The apparatus further includes an ultrasonic assembly positioned relative to the moving web such that the minimum distance between the ultrasonic horn at rest (e.g., prior to excitation) and the deformed surface of the web is from about 0.0005 to about 0.005 inch. The apparatus further includes a mechanism for controlling the amount of energy imparted to the ultrasonic assembly such that the ultrasonic assembly provides sufficient ultrasonic energy to the moving web to raise the surface temperature of the deformed surfaces to slightly above the melting temperature of the web only in the areas where the image is to be formed.

In yet another embodiment of the present invention, there is provided an apparatus for forming an absorbent garment having an image thereon, the apparatus including a mechanism for supplying top sheet material, a mechanism for supplying back sheet material, and a mechanism for supplying an absorbent core. The apparatus also includes a forming station for bringing the back sheet material, top sheet material and absorbent core into engagement with one another by disposing the absorbent core between the top sheet material and the back sheet material.

The apparatus also includes a mechanism for transporting a web past an ultrasonic assembly, an imaging roll capable of deforming the surface of the web without punching holes there through, whereby the deformed surface corresponds to either a positive or a negative of the image to be formed. The apparatus further includes an ultrasonic assembly positioned relative to the moving web such that the minimum distance between the ultrasonic horn at rest (e.g., prior to excitation) and the deformed surface of the web is from about 0.0005 to about 0.005 inch. The apparatus further includes a mechanism for controlling the amount of energy imparted to the ultrasonic assembly such that the ultrasonic assembly provides sufficient ultrasonic energy to the moving web to raise the surface temperature of the deformed surfaces to slightly above the melting temperature of the web only in the areas where the image is to be formed.

In one embodiment, the moving web is the back sheet material, and the ultrasonic assembly is disposed in the machine direction either prior to, or after the forming station. In another embodiment, the web is an applique layer, the ultrasonic assembly is disposed in a position independent from the forming station, and the apparatus further includes a mechanism for cutting and disposing the applique layer containing the image on the back sheet material either prior to, or after the back sheet material travels through the forming station.

These and other objects, features and advantages of the preferred embodiments will become readily apparent upon reading of the detailed description of the preferred embodiments of this invention in conjunction with the following drawings.

DETAILED DESCRIPTION OF THE PREFERRED EMBODIMENTS

Figure 1:
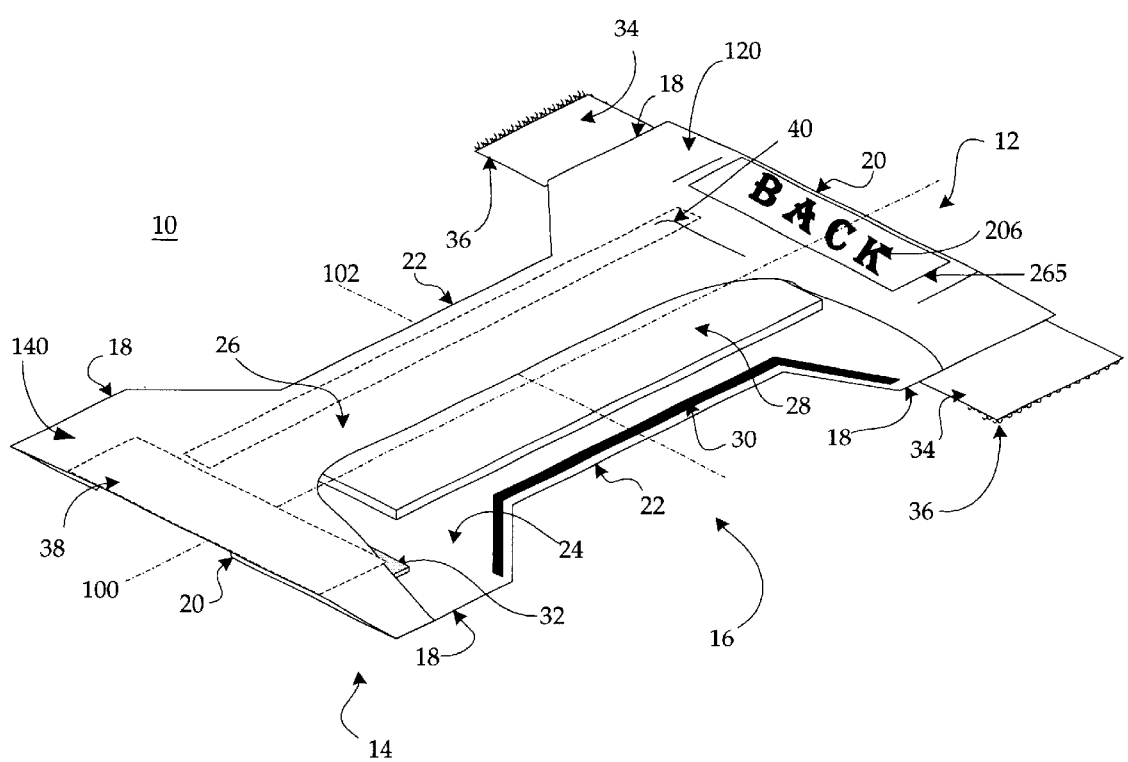
FIG. 1 is an exploded view of an embodiment of the present invention with elastic members shown in the elongated position for clarity, and the garment laid flat.

As used herein, the term "absorbent garment" or "absorbent article" refers to garments that absorb and contain exudates, and more specifically, refers to garments which are placed against or in proximity to the body of the wearer to absorb and contain the various exudates discharged from the body. A non-exhaustive list of examples of absorbent articles includes diapers, diaper covers, disposable diapers, training pants, feminine hygiene products, and adult incontinence products. The term "disposable absorbent garment" refers to absorbent garments that are intended to be discarded or partially discarded after a single use (i.e., they are not intended to be laundered or otherwise restored or reused).

The present invention can be used with all of the foregoing classes of absorbent articles, without limitation, whether disposable or otherwise. These classifications are used interchangeably throughout the specification, but are not intended to limit the claimed invention. The invention will be understood to encompass, without limitation, all classes and types of absorbent articles, including those described above.

The term "component" can refer, but is not limited, to designated selected regions, such as edges, corners, sides or the like; structural members, such as elastic strips, absorbent pads, stretchable layers or panels, layers of material, or the like; or a graphic. The term "graphic" can refer, but is not limited, to any design, pattern, indicia or the like.

Throughout this description, the term "disposed" and the expressions "disposed on," "disposing on," "disposed in," and variations thereof (e.g., a description of the article being "disposed" is interposed between the words "disposed" and "on") are intended to mean that one element can be integral with another element, or that one element can be a separate structure bonded to or placed with or placed near another element. Thus, a component that is "disposed on" an element of the absorbent garment can be formed or applied directly or indirectly to a surface of the element, formed or applied between layers of a multiple layer element, formed or applied to a substrate that is placed with or near the element, formed or applied within a layer of the element or another substrate, or other variations or combinations thereof.

Throughout this description, the terms "top sheet" and "back sheet" denote the relationship of these materials or layers with respect to the absorbent core. It is understood that additional layers may be present between the absorbent core and the top sheet and back sheet, and that additional layers and other materials may be present on the side opposite the absorbent core from either the top sheet or the back sheet.

The present invention preferably includes a method of making absorbent articles, wherein each absorbent article has an image either formed directly on a moving web that forms a part of the article, or on an appliqué layer that then is subsequently adhered to, disposed on, or otherwise associated with the absorbent article. The method includes imparting sufficient ultrasonic energy with an ultrasonic horn to the moving web or appliqué layer to raise the surface temperature of the moving web to slightly above the melting temperature of the moving web (or appliqué layer) only in the areas where the image is to be formed, to thereby form the image. In accordance with the method, when excited, the ultrasonic horn vibrates transversely to the direction of the moving web or appliqué layer, and does not come into contact with the material that is imaged prior to excitation.

During operation and when the ultrasonic horn is excited and begins vibrating, the horn only contacts the image areas of the moving web briefly such that holes are not formed in the web. It is particularly preferred in the invention that the amount of energy imparted by the ultrasonic horn be controlled to prevent forming a hole in the web or appliqué layer that can be caused by melting all the way through the material. While not intending on being bound by any theory of operation, it is believed that imparting too much energy to the moving web may cause sufficient thermal degradation of the integrity of the web to cause destruction and hole formation while tension is applied to the moving web. In addition, it is believed that contacting the ultrasonic horn and the moving web for too long may create undesirable stress and strain on the moving web and consequently form holes therein.

The absorbent article of the invention preferably has a front waist region, a rear waist region and a crotch region positioned between the front and rear waist regions. The front waist region and rear waist region can be associated with one another to form a waist opening, and two leg openings. Those skilled in the art recognize that "front" and "rear" in the context of the invention denote for clarity purposes only the front and rear of a user, and that the absorbent article could be reversed whereby the previously described "front" portion becomes the rear portion, and vice versa.

Leg elastics preferably are provided along the leg openings for securely holding the leg openings against the thighs of the wearer to improve containment and fit. A fastening system, either re-sealable or permanent, preferably holds the absorbent article around the wearer's waist. The fastening system assists in associating the front waist region with the rear waist region. A pair of stand-up leg gathers or waist containment flaps may be attached to or formed from the body's side surface of the top sheet.

The invention now will be described with reference to the attached drawings illustrating preferred embodiments of the invention. For clarity, features that appear in more than one Figure have the same reference number in each Figure.

FIG. 1 is a partially cut away depiction of an exemplary embodiment of an absorbent garment 10 (preferably a disposable absorbent garment) of the present invention. The embodiment shown in FIG. 1 is an infant's diaper, however, this depiction is not intended to limit the invention, and those skilled in the art appreciate that the invention covers other types of absorbent articles. For simplicity, however, the invention will be described with reference to an infant's diaper. The garment 10 of FIG. 1 is depicted in a generally flattened position, with the body-facing side facing down, and with the various elastic components depicted in their relaxed condition with the effects of the elastics removed for clarity (when relaxed, the elastics typically cause the surrounding material to gather or "shirr"). In the flattened position, the garment 10 may have a generally hourglass shaped structure, but it may also have any other shape suitable for the given application, such as a rectangular shape, a trapezoidal shape, a "T" shape, and the like.

As used herein, the longitudinal axis 100 of the garment is the dimension of the garment corresponding to the front-to-rear dimension of the user, and the lateral axis 102 of the garment is the dimension corresponding to the side-to-side dimension of the user.

In use, the invention comprises a pant-like garment 10 having a waist-encircling region and a crotch region. The waist-encircling region may comprise a first waist region 12, disposed adjacent to, for example, the back waist region of a wearer's body, and a second waist region 14, disposed adjacent to, for example, the front waist region of a wearer's body. The first and second waist regions 12, 14, may correspond to the front and back of the wearer's body, respectively, depending on whether garment 10 is attached in front of or behind the subject wearer. The first and second waist regions are joined together at or near their lateral edges 18, causing the longitudinally distal edges 20 of the garment 10 to form the perimeter of a waist opening. A crotch region 16 extends between the first and second waist regions 12, 14, and the crotch edges 22 form the perimeter of a pair of leg openings, when the garment 10 is placed on a subject wearer.

The garment 10 preferably comprises a top sheet 24, and a back sheet 26, which may be substantially coterminous with the top sheet 24. When the garment 10 is being worn, the top sheet 24 faces the wearer's body, and the back sheet 26 faces away from the wearer. An absorbent core 28 preferably is disposed between at least a portion of the top sheet 24 the back sheet 26.

An embodiment of the present invention may further comprise various additional features. One or more pairs of elastic gathers 30 may extend adjacent the crotch edges 22. The garment 10 may also comprise one or more waste containment systems, such as inboard standing leg gathers 40, which preferably extend from the second waist region 14 to the first waist region 12 along opposite sides of longitudinal center line 100 (only one standing leg gather system 40 is shown in FIG. 1 for purposes of clarity). One or both of the first and second waist regions 12, 14 may also be equipped with strips of elastic waist foam 32 or other elastically extensible material, which help contract the garment around the wearer's waist, providing improved fit and leakage prevention.

The absorbent garment 10 also preferably includes fastening elements to enable attachment of the first waist region 12 to second waist region 14. Fastening elements preferably include a pair of tabs 34 that extend laterally away from opposite lateral edges 18 of the first waist region 12 of the garment 10. The tabs 34 may comprise an elastically extensible material (not shown), and may be designed to stretch around a wearer's waist to provide improved fit, comfort, and leakage protection. Such elasticized tabs 34 may be used in conjunction with, or in lieu of, waist foam 32, or other elastically extensible materials 32.

At least one fastening mechanism 36 (collectively referred to as "fastener 36") is attached to each tab 34 for attaching the tab to the second waist region 14, thereby providing the garment 10 with a pant-like shape, and enabling garment 10 to be fixed or otherwise fitted on the wearer. The fasteners 36 may attach to one or more target devices 38 located in the second waist region 14.

Although not shown in the drawings, the absorbent garment 10 may also include grips attached along one of its edges proximal to each tab 34 to enable a caregiver to pull the grips, and not on the ends of the tabs 34, around the wearer and over the target devices 38 to thereby secure the fasteners 36 to the one or more target devices 38.

The various parts of the garment 10 can be attached to one another or associated with one another to form a structure that preferably maintains its shape during the useful life of the garment 10. As used herein, the terms "attached," "joined," "associated," and similar terms encompass configurations whereby a first part is directly joined to a second part by affixing the first part directly to the second part, by indirectly joining the first part to the second part through intermediate members, and by fixing the relative positions of various parts by capturing parts between other parts. Those skilled in the art will appreciate that various methods or combinations of methods may be used to securely join the respective parts of the garment 10 to one another.

The top sheet 24 and back sheet 26 may be constructed from a wide variety of materials known in the art. The invention is not intended to be limited to any specific materials for these components. The top sheet 24 and back sheet can be shaped and sized according to the requirements of each of the various types of absorbent garment, or to accommodate various user sizes. In an embodiment of the invention in which the garment 10 is a diaper or an adult incontinence brief, the combination of top sheet 24 and back sheet 26, may have an hourglass shape, as seen in FIG. 1, or may have a rectangular, trapezoidal, "T" shape, or other shape.

Due to the wide variety of backing and liner sheet construction and materials currently available, the invention is not intended to be limited to any specific materials or constructions of these components. The back sheet 26 preferably is made from any suitable pliable liquid-impervious material known in the art. Typical back sheet materials include films of polyethylene, polypropylene, polyester, nylon, and polyvinyl chloride and blends of these materials. For example, the back sheet can be made of a polyethylene film having a thickness in the range of 0.02–0.04 mm. The back sheet 26 may be pigmented with, for example, titanium dioxide, to provide the garment 10 with a pleasing color or to render the back sheet 26 opaque enough that exudates being contained by the garment 10 are not visible from outside the garment. In addition, the back sheet 26 may be formed in such a manner that it is opaque, for example, by using various inert components in the polymeric film and then biaxially stretching the film. Other back sheet materials will be readily apparent to those skilled in the art. The back sheet 26 preferably has sufficient liquid imperviousness to prevent any leakage of fluids. The required level of liquid imperviousness may vary between different locations on the garment 10.

The back sheet 26 may further comprise separate regions having different properties. In a preferred embodiment, portions of the back sheet 26 are air-permeable to improve the breathability, and therefore comfort, of the garment 10. The different regions may be formed by making the back sheet 26 a composite or laminate of different sheet materials, chemical treatment, heat treatment, or other processes or methods known in the art.

Some regions of the back sheet 26 may be fluid pervious. In one embodiment of the invention, the back sheet 26 is fluid impervious in the crotch 16, but is fluid pervious in portions of the first and second waist regions 12, 14.

If an image is directly formed on the back sheet 26 of the invention, it is preferred that the back sheet be constructed of a non-woven fibrous web that is capable of thermoplastic deformation upon application of ultrasonic energy. Particularly preferred non-woven fibrous webs include a spun-bonded non-woven web of synthetic fibers such as polypropylene, polyethylene or polyester fibers; a non-woven web of cellulosic fibers, textile fibers such as rayon fibers, cotton and the like, or a blend of cellulosic and textile fibers; a spun-bonded non-woven web of synthetic fibers such as polypropylene; polyethylene or polyester fibers mixed with cellulosic, pulp fibers, or textile fibers; or melt blown thermoplastic fibers, such as macro fibers or micro fibers of polypropylene, polyethylene, polyester or other thermoplastic materials or mixtures of such thermoplastic macro fibers or micro fibers with cellulosic, pulp or textile fibers. For example, the back sheet can be made of a non-woven fibrous sheet having a thickness in the range of 0.0005–0.005 inch.

The moisture-pervious top sheet 24 can be comprised of any suitable relatively liquid-pervious material known in the art that permits passage of liquid there through. Non-woven liner sheet materials are exemplary because such materials readily allow the passage of liquids to the underlying absorbent laminate core 28. Examples of suitable liner sheet materials include non-woven spun-bond or carded webs of polypropylene, polyethylene, nylon, polyester and blends of these materials.

The back sheet 26 may be comprised of, or may be covered with a fibrous, non-woven fabric such as is disclosed, for example, in U.S. Pat. No. 4,646,362 issued to Heran et al., the disclosure of which is hereby incorporated by reference in its entirety and in a manner consistent with this disclosure. Materials for such a fibrous outer liner include a spun-bonded non-woven web of synthetic fibers such as polypropylene, polyethylene or polyester fibers; a non-woven web of cellulosic fibers, textile fibers such as rayon fibers, cotton and the like, or a blend of cellulosic and textile fibers; a spun-bonded non-woven web of synthetic fibers such as polypropylene; polyethylene or polyester fibers mixed with cellulosic, pulp fibers, or textile fibers; or melt blown thermoplastic fibers, such as macro fibers or micro fibers of polypropylene, polyethylene, polyester or other thermoplastic materials or mixtures of such thermoplastic macro fibers or micro fibers with cellulosic, pulp or textile fibers. Alternatively, the back sheet 26 may comprise three panels wherein a central poly back sheet panel is positioned closest to absorbent laminate core 28 while outboard non-woven breathable side back sheet panels are attached to the side edges of the central poly back sheet panel. Alternatively, the back sheet 26 may be formed from microporous poly cover stock for added breathability. The image of the invention can suitably be formed on any of these materials, including the fibrous, non-woven outer cover sheet.

The top sheet 24 may be formed of three separate portions or panels. Those skilled in the art will recognize, however, that top sheet 24 need not be made of three separate panels, and that it may be comprised of one unitary item. A first top sheet panel (not shown) may comprise a central top sheet panel formed from preferably a liquid-pervious material that is either hydrophobic or hydrophilic. The central top sheet panel may be made from any number of materials, including synthetic fibers (e.g., polypropylene or polyester fibers), natural fibers (e.g., wood or cellulose), apertured plastic films, reticulated foams and porous foams to name a few. One preferred material for a central top sheet panel or entire top sheet 24 is a cover stock of single ply non-woven material which may be made of carded fibers, either adhesively or thermally bonded, perforated plastic film, spun-bonded fibers, or water entangled fibers, which generally weigh from 0.3–0.7 oz./sq. yd. and have appropriate and effective machine direction and cross-machine direction strength suitable for use as a baby diaper cover stock material. The central top sheet panel preferably extends from substantially the second waist region 14 to the first waist region 12, or a portion thereof.

A second and third top sheet panel (e.g., outer top sheet panels, not shown), in this alternative embodiment may be positioned laterally outside of the central top sheet panel. The outer top sheet panels preferably are substantially liquid-impervious and hydrophobic, preferably at least in the crotch area. The outer edges of the outer top sheet panels may substantially follow the corresponding outer perimeter of the back sheet 26. The material for the outer top sheet portions or panels preferably is polypropylene and can be woven, non-woven, spun-bonded, carded or the like, depending on the application.

At the point of connection between the outer top sheet panels and the central top sheet panel, inner edges of the outer top sheet portions or panels may extend upwardly to form waste containment flaps 40. The waste containment flaps 40 preferably are formed of the same material as the outer top sheet portions or panels, as in the embodiment shown. The waste containment flaps 40 may be treated with a suitable surfactant to modify their hydrophobicity/hydrophilicity as desired, and they may be treated with skin wellness ingredients to reduce skin irritation. Alternatively, the waste containment flaps 40 may be formed as separate elements and then attached to the body side liner.

The waste containment flaps 40 preferably include a portion that folds over onto itself to form a small enclosure. At least one, and depending on the size of the enclosure sometimes more than one, elastic member may be secured in the enclosure in a stretched condition. As is well known in the art, when the flap elastic attempts to assume the relaxed, unstretched condition, the waste containment flaps 40 rise above the surface of the central top sheet portion or panel.

The top sheet 24 may be made of any suitable relatively liquid-pervious material currently known in the art or later discovered that permits passage of a liquid there through. Examples of suitable top sheet materials include non-woven spun-bonded or carded webs of polypropylene, polyethylene, nylon, polyester and blends of these materials, perforated, apertured, or reticulated films, and the like. Non-woven materials are exemplary because such materials readily allow the passage of liquids to the underlying absorbent core 28. The top sheet 24 preferably comprises a single-ply non-woven material that may be made of carded fibers, either adhesively or thermally bonded, spun-bonded fibers, or water entangled fibers, which generally weigh from 0.3–0.7 oz./sq. yd. and have appropriate and effective machine direction (longitudinal) and cross-machine (lateral) direction strength suitable for use as a top sheet material for the given application. The present invention is not intended to be limited to any particular material for the top sheet 24, and other top sheet materials will be readily apparent to those skilled in the art.

The top sheet 24 may further comprise several regions having different properties. In one embodiment of the present invention, the laterally distal portions of the top sheet 24, especially those used to make the outer top sheet panels preferably are substantially fluid impervious and hydrophobic, while the remainder of the top sheet 24 (e.g., central top sheet panel) is hydrophilic and fluid pervious. Different top sheet properties, such as fluid perviousness and hydrophobicity, may be imparted upon the top sheet 24 by treating the top sheet 24 with adhesives, surfactants, or other chemicals, using a composite of different materials, or by other means. The top sheet 24 may also be made from a laminate of overlaid sheets of material. The top sheet 24 also may be treated in specific areas like the crotch region, with skin wellness ingredients such as aloe, vitamin E, and the like.

As noted elsewhere herein, the top sheet 24 and back sheet 26 may be substantially coterminous, or they may have different shapes and sizes. The particular design of the top sheet 24 and back sheet 26 may be dictated by manufacturing considerations, cost considerations, and performance considerations. Preferably, the top sheet 24 is large enough to completely cover the absorbent laminate core 28, and the back sheet 26 is large enough to prevent leakage from the garment 10. The design of top sheet 24 and back sheet 26 is known in the art, and a skilled artisan will be able to produce an appropriate top sheet 24 and an appropriate back sheet 26 without undue experimentation.

The top sheet 24 and the back sheet 26 may be associated with one another using a variety of methods known in the art. For example, they may be thermally, ultrasonically, or chemically bonded to one another. They also may be joined using lines of hot melt adhesive or mechanical fasteners, such as thread, clips, or staples. In one embodiment, a hydrophilic adhesive, such as Cycloflex as sold by National Starch, a corporation headquartered in Bridgewater, N.J., is used to join the top sheet 24 to the back sheet 26. The particular joining method may be dictated by the types of materials selected for the top sheet 24 and back sheet 26.

As mentioned above, absorbent garment 10 preferably is provided with leg elastics 30 extending through crotch region 16, adjacent crotch edge 22. The absorbent garment of the invention also preferably is provided with waist elastic material 32 optionally in the first and second waist regions, 12, 14, respectively, to enable and assist in stretching around the wearer. The waist elastics 32 may be similar structures or different to impart similar or different elastic characteristics to the first and second waist regions 12, 14 of the garment. In general, the waist elastics may preferably comprise foam strips positioned at the first and second waist regions 12, 14, respectively. Such foam strips preferably are about ½ to about 1½ inches wide and about 3–6 inches long. The foam strips preferably are positioned between the top sheet 24 and the back sheet 26. Alternatively, a plurality of elastic strands may be employed as waist elastics rather than foam strips. The foam strips preferably are comprised of polyurethane, but can be any other suitable material that decreases waist band roll over, reduces leakage over the waist ends of the absorbent garment, and generally improve comfort and fit. The first and optional second waist foam strips 32 preferably are stretched 50–150%, preferably 100% more than their unstretched dimension before being adhesively secured between the back sheet 26 and top sheet 24 or before being secured between two materials, preferably non-woven materials.

Each edge 22 that forms the leg openings preferably is provided with an adjacent leg elastic containment system 30. In the preferred embodiment, three strands of elastic threads are positioned to extend adjacent to leg openings between the top sheet 24 and the back sheet 26. Any suitable elastomeric material exhibiting at least an elongation (defined herein as $(L_S-L_R)/L_R$ where $L_S$ is the stretch length of an elastic element and LR is retracted length, multiplied by 100 to obtain percent elongation) in the range of 5%–350%, preferably in the range of 200%–300%, can be employed for the leg elastics 30. The leg elastics 30 may be attached to the absorbent article 10 in any of several ways which are known in the art. For example, the leg elastics 30 may be ultrasonically bonded, heat/pressure sealed using a variety of bonding patterns, or glued to the garment 10. Various commercially available materials can be used for the leg elastics 30, such as natural rubber, butyl rubber or other synthetic rubber, urethane, elastomeric materials such as LYCRA (DuPont), GLOSPAN (Globe) or SYSTEM 7000 (Fulflex).

The fastening elements, preferably a fastening system 34 (e.g., tab 34) of the preferred embodiment, is attached to the first waist region 12, and it preferably comprises a tape tab or mechanical fasteners 36. However, any fastening mechanism known in the art will be acceptable. Moreover, the fastening system 34 may include a reinforcement patch below the front waist portion so that the diaper may be checked for soiling without compromising the ability to reuse the fastener. Alternatively, other absorbent article fastening systems are also possible, including tapes, adhesives, safety pins, buttons, and snaps.

As stated previously, the invention has been described in connection with a diaper. The invention, however, is not intended to be limited to application only in diapers. Specifically, the absorbent cores of the preferred embodiments may be readily adapted for use in other absorbent garments besides diapers, including, but not limited to, training pants, feminine hygiene products and adult incontinence products. Indeed, given the enhanced thermal transmittance, the absorbent articles of the present invention are particularly suitable for use in adult incontinence products and feminine hygiene products.

The underlying structure beneath the top sheet 24 may include, depending on the diaper construction, various combinations of elements, but in each embodiment, it is contemplated that the absorbent garment will preferably include an absorbent core 28. For example, additional layers may be disposed between the top sheet 24 and absorbent core 28, and/or other additional layers may be disposed between these layers, or between absorbent core 28 and back sheet 26. The additional layer(s) may include a fluid transfer layer, a fluid handling layer, a storage layer, a wicking layer, a fluid distribution layer, and any other layer(s) known to those having ordinary skill in the art.

Although the absorbent core 28 depicted in FIG. 1 has a substantially rectangular cross-sectional and plan view shape, other shapes may be used, such as a "T" shape or an hourglass shape. The shape of the absorbent core 28 may be selected to provide the greatest absorbency with a reduced amount of material. The absorbent core may be associated with the top sheet 24, back sheet 26, or any other suitable part of the garment 10 by any method known in the art, in order to fix the absorbent core 28 in place. In addition to the respective layers in the absorbent core 28, as will be described in greater detail hereinafter, the overall absorbent core 28 may be enclosed within a tissue wrapping, as disclosed in U.S. Pat. No. 6,068,620, the disclosure of which is incorporated by reference herein in its entirety. Skilled artisans are capable of designing and wrapping a suitable absorbent core 28 of the invention, using the guidelines provided herein.

Any suitable absorbent material may be used for absorbent core 28. Absorbent cores containing a mixture of fibrous material and superabsorbent polymers (SAP) are well known in the art and described, for example, in U.S. Pat. No. 5,281,207, to Chmielewski, and U.S. Pat. No. 5,863,288, to Baker, the disclosures of each of which are herein incorporated by reference in their entirety and in a manner consistent with this disclosure. The fibrous material can be any fibrous material, preferably one that is capable of absorbing fluids and capable of retaining SAP particles within its matrix. Preferred fibrous materials may be selected from cellulose acetate fibers, rayon fibers, Courtauld's LYOCELL fibers, polyacrylonitrile fibers, surface-modified (hydrophilic) polyester fibers, surface-modified polyolefin/polyester bicomponent fibers, surfacemodified polyester/polyester bicomponent fibers, cotton fibers, or blends thereof. In addition, rayon, Courtauld's LYOCELL, polyacrylonitrile, cotton fibers and cotton linters are alternatively preferred. The remaining fibers, surface-modified polyolefin/polyester bicomponent fibers, and surface-modified polyester/polyester bicomponent fibers are also believed to be effective fibrous materials for use in the invention.

Any superabsorbent polymer (SAP) now known or later discovered may be used in absorbent core 28, so long as it is capable of absorbing liquids. Useful SAP materials are those that generally are water-insoluble but water-swellable polymeric substance capable of absorbing water in an amount that is at least ten times the weight of the substance in its dry form. In one type of SAP, the particles or fibers may be described chemically as having a back bone of natural or synthetic polymers with hydrophilic groups or polymers containing hydrophilic groups being chemically bonded to the back bone or in intimate admixture therewith. Included in this class of materials are such modified polymers as sodium neutralized cross-linked polyacrylates and polysaccharides including, for example, cellulose and starch and regenerated cellulose which are modified to be carboxylated, phosphonoalkylated, sulphoxylated or phosphorylated, causing the SAP to be highly hydrophilic. Such modified polymers may also be cross-linked to reduce their water-solubility.

The absorbent article 10 of the present invention preferably has a graphic 206 formed thereon. Graphic image 206 can be comprised of any image, such as lettering, as shown in FIG. 1, or characters, such as any and all of those described in, for example, U.S. Pat. Nos. 6,307,119 and 6,297,424, the disclosures of which are incorporated by reference herein in their entirety. The graphic 206 may be formed directly on the back sheet 26, on an outer non-woven fibrous material, or on an appliqué layer 265, preferably a non-woven strip appliqué layer 265, and then cut and placed on back sheet 26 or other outer material by methods known to those skilled in the art.

The various methods of forming the image either directly on back sheet 26 or on an appliqué layer 265, or on some other web material will be described with reference to FIGS. 2–8. Stated generally, the method includes using an ultrasonic horn to impart sufficient ultrasonic energy to a moving web or appliqué layer to raise the surface temperature of the moving web to slightly above the melting temperature of the moving web or appliqué layer only in the areas where the image is to be formed, to thereby form the image. In accordance with the method, the ultrasonic horn vibrates in a direction generally orthoganol, or perpendicular to the direction of the moving web or appliqué layer, and does not come into contact with the material that is imaged when the ultrasonic horn is at rest (prior to excitation). It is particularly preferred in the invention that the amount of energy imparted by the ultrasonic horn be controlled to prevent forming a hole in the web or appliqué layer. Those skilled in the art will recognize that holes can be formed in a moving web or non-woven fibrous appliqué layer by failing to adequately control the amount of energy imparted to the web.

Various embodiments of apparatus used for imparting a graphic to a moving web are shown FIGS. 2–5. The apparatus generally includes a mechanism for transporting a web of material containing at least one thermoplastic fiber in a machine direction and past an ultrasonic horn, an imaging roll capable of deforming the surface of the web without punching holes there through, whereby the deformed surface corresponds to the image to be formed. The apparatus further includes an ultrasonic horn positioned relative to the moving web such that the minimum distance (item "d" in FIGS. 6a and 6b) between the ultrasonic horn, when at rest and prior to excitation and the deformed surface of the web, is from about 0.0005 to about 0.005 inch. The apparatus further includes a mechanism for controlling the amount of energy imparted to the ultrasonic horn such that the horn provides sufficient ultrasonic energy to the moving web to raise the surface temperature of the raised surfaces to slightly above the melting temperature of the web only in the areas where the image is to be formed to thereby form the image.

Figure 2:
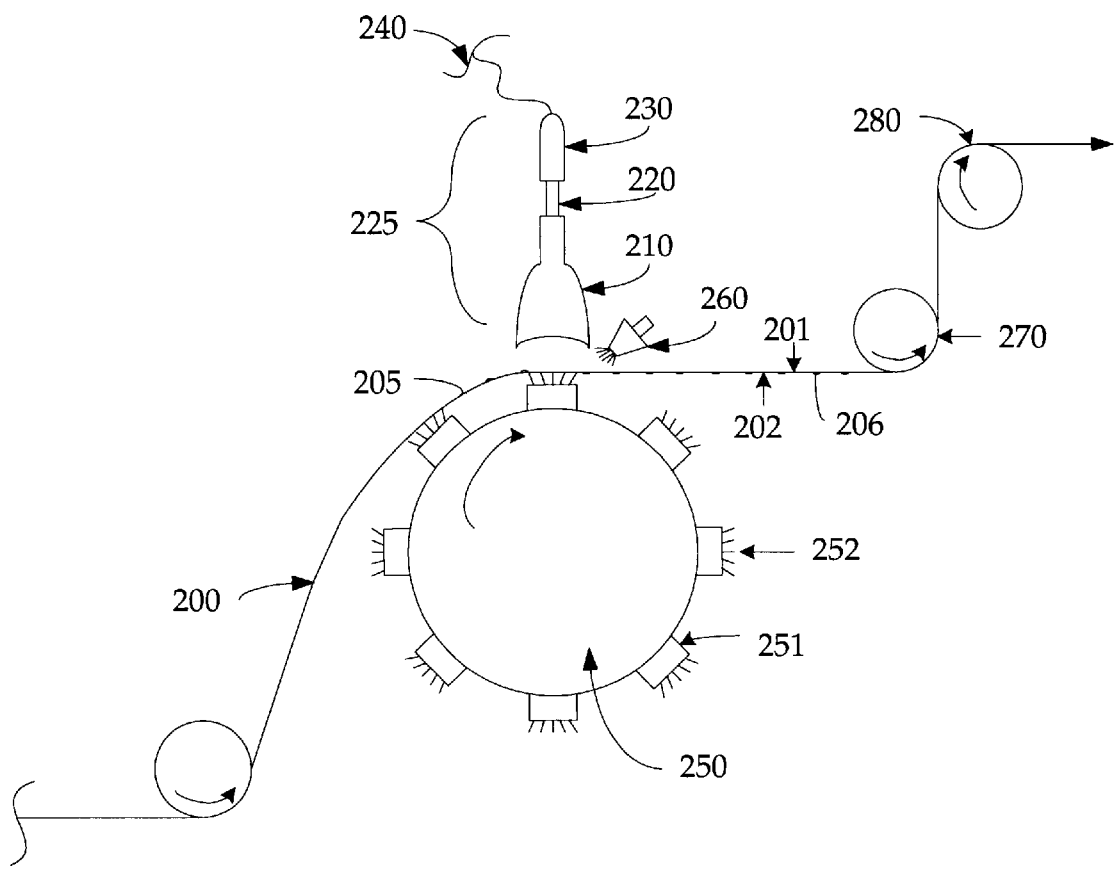
FIG. 2 is a schematic of one embodiment of an apparatus useful in forming an image on a moving web.

FIG. 2 illustrates one method and apparatus for forming such an image. Web material 200 (e.g., back sheet 26, appliqué layer 265, outer non-woven fibrous sheet, or other web material) is fed to the ultrasonic assembly 225 by any mechanism (not shown) capable of feeding a web of material. Various mechanisms capable of feeding and of transporting web 200 past ultrasonic assembly 225 include pinch rollers, nip rollers, endless belts, vacuum drawing devices, feed rollers, extruding apparatus, conveyor systems, belt and motor drive conveying systems, and equivalents thereof.

Ultrasonic assembly 225 can be any assembly capable of imparting ultrasonic energy (preferably in a controlled manner) to a moving web. It is particularly preferred that ultrasonic assembly apply sufficient energy in relatively precise locations to enable precise melting of the web material, and not create holes through the web. The particular apparatus or assembly 225 employed is not critical to the invention.

A useful ultrasonic assembly 225 for the present invention includes a vibratory tool or horn 210, preferably coupled to one or more transducers 230, which may be a piezoelectric transducer, via booster 220. Energy applied to horn 210 creates resonance of the horn at frequencies and amplitudes so that horn 210 vibrates rapidly in a direction generally perpendicular to the machine direction of the moving web 200. Vibration of horn 210 generates heat near the surface of the horn, which enables precise application of heat in areas only where horn 210 comes near or engages a surface of the moving web 200. Booster 220 enables some control of the amplitude and frequency of vibration by amplifying or "boosting" the amount of power supplied from transducer 230 to horn 210. For example, if booster 220 permits the power to be amplified by 1–2 times, one can control the amount of power supplied to transducer 230 in a manner such that the ultimate power supplied to horn 210 is adequate to provide the precise amount of energy.

Suitable ultrasonic assembly devices 225 are disclosed, for example, in U.S. Pat. Nos. 3,113,225, 3,562,041, 3,733,238, and 6,036,796, the disclosures of each of which are incorporated by reference herein in their entirety. Ultrasonic assembly 225 preferably is connected to a controlling mechanism 240 capable of controlling the amount of energy supplied to ultrasonic assembly 225. Any type of power controller can be used, including, for example, generators, transducers, closed-loop feedback system disclosed in U.S. Pat. No. 6,036,796, electroacoustic transducers, and the like. Controlling mechanisms 240 include computerized systems capable of varying the amount of power supplied to transducer 230, manually controllable power supplies, and the like. Those skilled in the art are capable of designing a suitable controlling mechanism 240, using the guidelines provided herein. Suitable ultrasonic assembly devices also may be purchased from Branson Electronics, Danbury, Conn., Hermann Ultraschalltechnik GmbH, D-76307, Karlsbad, Germany, or Dukane Corporation, Saint Charles, Ill.

Ultrasonic assembly manufacturers and dealers typically distribute the assembly in component parts, such as transducers 230, boosters 220, and horns 210. Horns 210 are available in a variety of geometric configurations, and the invention is not particularly limited to any particular geometry. It is preferred that the geometry of the horn be designed so as to provide minimal tension on moving web 200 when it periodically engages the moving web during excitation. The particular design of the ultrasonic assembly 225 is within the skill of an ordinarily skilled artisan, using the guidelines provided herein. For example, given the line speed of moving web 200, the size of deformations 205, the make-up of moving web 200, one can readily determine the requisite amount of energy needed to raise the surface temperature of the deformed web to slightly above its melting temperature. The ultrasonic assembly 225 then can be designed using the amount of energy needed, the geometry of the horn 210, the speed of moving web 200, and the minimum distance "d" (see, FIGS. 6a and 6b).

Because heat is generated by vibrating horn 210, it is preferred to cool moving web 200 prior to or after forming the image. Any mechanism 260 capable of cooling the web 200 can be used in the invention, including spraying or applying cool air or fluid (e.g., water, solvent, etc.) on the web, using cooling drums or chill rolls, and the like. The embodiment depicted in FIG. 2 illustrates a particularly preferred method of cooling web 200, by using spray nozzle 260 to spray cool liquid on web 200. The heat generated by vibrating horn 210 typically is great enough to flash any residual liquid from the surface of the web 200 so that the web is dry for downstream processing. Spray nozzle 260 also could be directed on horn 210 or other portions of ultrasonic assembly 225, in addition to or as a substitute for spray nozzle 260 shown in FIG. 2.

Web 200 may be transported past ultrasonic assembly 225 via pinch or nip rollers 270, 280, or a suitable web supply mechanism, which ordinarily would be disposed upstream from ultrasonic assembly 225. Pinch rollers are well known in the art, and can be composed of any suitable material (steel, rubber, etc.), and can be designed to transport web 200 at any suitable speed, either constantly or at varying speeds. Image 206 may be imparted to web 200 using any of a variety of techniques used to emboss webs. For example, a patterned anvil 250 may be used to deform web 200, for example, by producing small projections or bumps 205 (FIGS. 6a and 6b) in web 200, which in turn are melted (either partially or fully) by the ultrasonic energy produced by ultrasonic apparatus 225. Patterned anvils are well known in the art, and described, for example, in U.S. Pat. Nos. 4,323,068, 5,599,420, and 6,165,298, the disclosures of which are incorporated by reference herein in its entirety. Patterned anvil may be comprised of projections 251 intermittently disposed about its circumference which contact and deform moving web 200 to impart the projections. It is particularly preferred that projections 251 include the particular graphic (text, picture, etc.) as raised elements 252 disposed on the exterior surface of projections 251.

The image can be formed by raised elements 252 engaging the undersurface 202 of web 200 to deform the web (e.g., create bumps or projections 205) in precise locations that either form a positive or negative image on the web upper surface 201. These deformations then are exposed to ultrasonic energy via ultrasonic assembly 225 and horn 210, and essentially melt (either partially or fully) only in the precise area where the web was deformed. While not intending on being bound by any theory, the present inventors believe that because the overall amount of ultrasonic energy imparted to web 200 is controlled by controlling the distance between horn 210 and deformations 205 (distance "d" in FIGS. 6a and 6b), the amount of energy or power supplied to horn 210, the speed of the moving web 200, the chemical make-up of web 200, and other factors described below, only the deformed portions 205 of the web 200 will melt and further deform to form impressions or depressions 206, which form the image. This forms a precise image in the moving web 200. The inventors also believe (again, not wishing to be bound by any theory of operation) that deformation of web 200 by patterned anvil 250 may deform the web in such a manner in these particular locations so as to slightly lower its melting point. Thus, the energy generated by ultrasonic assembly 225 as deformations 205 move there under serves to only melt the deformations 205, but not the remaining portion of the web.

Moving web 200 may be comprised of a material that is rendered translucent and/or transparent by the deformation and formation of image 206 and preferably is comprised of a material containing at least one thermoplastic material. For example, web 200 may be comprised of a translucent or opaque film of non-woven or spun bonded polyolefin (e.g., polyethylene, polypropylene, polybutylene, and mixtures and copolymers thereof). Web 200 also may be comprised of a laminated material comprised of a number of different layers. In addition, web 200 may be comprised of a substrate that can be printed and then applied to backsheet 26 or other non-woven outer cover sheets. Such a substrate is referred to herein as an appliqué layer. When melted in precise locations to form image 206, the small melted dots (or large depressions), may become transparent or translucent. A multicolored image therefore can be obtained by placing a colored film beneath web 200 so that one or more colors can be seen through the melted areas 206, but not through the remaining portions of web 200. Methods of using transparent or translucent windows in outer covers of absorbent articles to reveal a wetness indicator or a different colored article, and the like, are described in U.S. Pat. Nos. 5,897,541 and 6,075,178, the disclosures of which are incorporated by reference herein in their entirety.

In a particularly preferred embodiment of the invention, the moving web is comprised of a non-woven polymeric material made from spun-bonded polypropylene fibers. Such a material is commercially available from First Quality Non-Wovens, Hazelton, PA. The moving web can be transported at a speed on the order of about 50 to about 500 m/min., preferably from about 100 to about 300 m/min., and most preferably from about 140 to about 175 m/min. It is most preferred that the moving web be transported at a speed of about 150 m/min. A patterned anvil roller similar to patterned anvil 250 can be used to form an image on the moving web. A suitable patterned anvil roller can have any diameter to allow it to rotate at a sufficient rate of speed to imprint the design on the moving web. The patterned anvil 250, projections 251 and other anvils (255, 257, 258) used in the process and apparatus of the invention can be made from any suitable material that will enable them to imprint a design on the moving web, without significantly deforming the web to the extent that, when subjected to ultrasonic imaging, holes or rips are formed in the web. It is preferred that the anvils be comprised of a hard material such as hardened steel and the like, and that the projections 251 be comprised of a more resilient material, such as rubber, impact copolymers, block copolymers, and the like. Those skilled in the art are capable of designing a suitable anvil roller and projections to impart an image on the moving web, using the guidelines provided herein.

Any ultrasonic assembly 225 can be used to impart the precise amount of energy to the moving web. A particularly preferred ultrasonic assembly 225 includes a transducer 230, a booster 220, and an ultrasonic horn 210.

To impart the precise amount of energy (e.g., heat) to the moving web, the skilled artisan will appreciate that a number of variables may be considered. These variables include the chemical and physical make-up of the moving web 200, the amount of deformation caused by patterned anvil 250, the distance "d" between the lowest point of movement of ultrasonic horn 210 when rested, and the deformations 205, the amount of energy or power supplied to horn 210, the degree of cooling, if any, imparted to web 200 via cooling apparatus 260, the thickness of moving web 200, and others. Using the guidelines provided herein, skilled artisans are capable of determining which variables require adjustment, and how to adjust and control the requisite variables to ensure the precise amount of energy applied to the moving web. Upon determining the amount of energy needed, as well as some other variables noted above, one can obtain the particular ultrasonic assembly 225 (transducer 230, booster 220 and horn 210) from suitable suppliers such as Branson Electronics, Danbury, Connecticut.

The amount of energy imparted to moving web 200 via ultrasonic assembly 225 can be controlled by any mechanism known in the art, and by any mechanism described in the aforementioned documents incorporated by reference herein, and preferably includes a variable power supply. The controlling mechanism also can be capable of determining the appropriate amount of energy imparted by ultrasonic assembly 225 by any one or combinations of the variables described immediately above. It is preferred that the amount of energy be controlled by controlling the amount of power provided to the assembly 225, and thus, the frequency and amplitude (e.g., intensity) of vibrations of ultrasonic horn 210.

For the moving web described above, which preferably is transported at or about 150 m/min., it is particularly preferred that the distance "d" between the lowest point of movement of ultrasonic horn 210 when at rest and prior to excitation, and the deformations 205 of web 200 be within the range of from about 0.0001 inch to about 0.01 inch, preferably from about 0.00025 inch to about 0.0075 inch, and most preferably from about 0.0005 inch to about 0.05 inch. It also is preferred that the ultrasonic assembly 225 be designed so that ultrasonic horn 210 vibrates at a frequency of about 20 to 40 KHz, and at an amplitude of from about 10 to about 120 $\mu$m. It also is particularly preferred that power be supplied from a controllable variable power supply 240 to transducer 230 at a rate of about 1000 amp, and that the booster 220 be capable of boosting the power within the range of from 0.6:1 to about 2.5:1, and most preferably from about 0.6:1 to about 1:1. Horn 210 preferably has a geometry that corresponds to the geometry of the patterned anvil 250, and is comprised of Al or Ti, or mixtures thereof.

While specific examples are described above with reference to particularly preferred embodiments, skilled artisans will appreciate that the amount of energy imparted by ultrasonic assembly 225 to moving web 200 will vary. Using the guidelines provided herein, those skilled in the art are capable of controlling the amount of energy imparted to moving web 200, without undue experimentation. The amount of energy imparted is controlled depending on, inter alia, the chemical make-up and speed of moving web 200, the distance "d", etc., so that the ultrasonic assembly 225 generates the requisite amount of energy to create the image by employing any one or combinations of the factors described above.

While not intending to be bound by any theory of operation, it is believed that an image can be formed in moving web 200 by imparting sufficient energy to deformations 205 to only partially melt, and not fully melt the material where the deformations exist (or where they don't exist for a negative image). Partially melted in this context denotes a state in which the material has not assumed a fully liquid state throughout the thickness of the material in the specific areas in which the deformations exist. Thus, the force applied to the moving web 200 in the machine direction by its being transported through the imaging area causes the partially melted areas to move, or stretch, or otherwise deform to a degree greater than the un-melted areas. These greater deformed areas correspond to the image for a positive image, or the un-deformed areas correspond to the image for a negative image.

Figure 3:
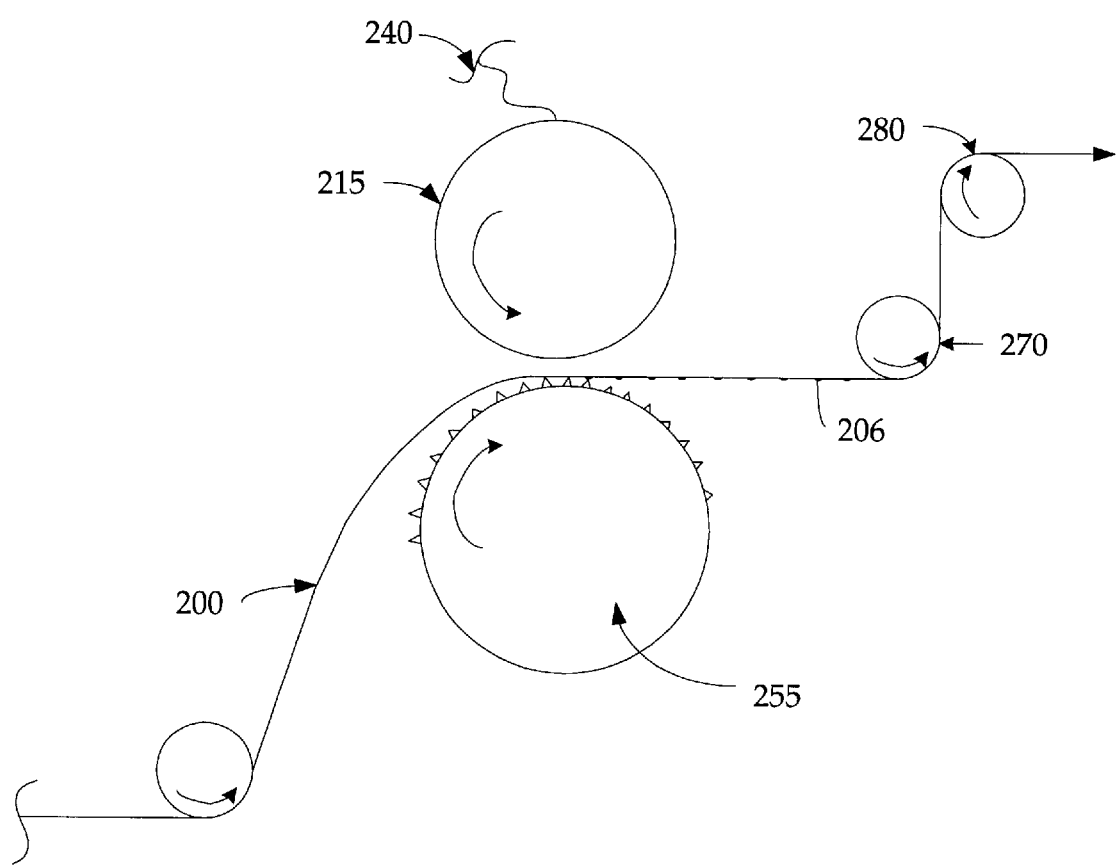
FIG. 3 is a schematic of another embodiment of an apparatus useful in forming an image on a moving web.

Other apparatus and methods suitable for forming an image in accordance with the present invention are illustrated in FIGS. 3–5 and 8. Turning now to FIG. 3, moving web 200 is transported past ultrasonic rotary horn 215 where it passes between the ultrasonic rotary horn 215 and patterned anvil 255. In this embodiment, as well as in other embodiments, any of the patterned anvils 250, 255, patterned rollers 257, ultrasonic rotary horn 215, and the like may be stationary (not rolling or rotating, but may vibrate transversely to web machine direction), may rotate freely as web 200 is moved by, or may be powered or driven to rotate. Ultrasonic rotary horns 215 are known in the art, and described, for example, in U.S. Pat. Nos. 5,096,532, and 5,110,403, the disclosures of which are incorporated by reference herein in their entirety.

Feed rollers or nip rollers 270, 280 can serve to transport moving web 200 past the ultrasonic rotary horn 215 and patterned anvil 255. The amount of energy imparted by ultrasonic rotary horn 215 can be controlled by controller/generator 240, or any other control mechanism capable of controlling the amount of power supplied to a powered apparatus, using techniques known in the art. Again, using the guidelines provided herein, a person skilled in the art is capable of varying the amount of energy ultrasonic rotary horn 215 will impart on moving web 200 without undue experimentation.

Figure 4:
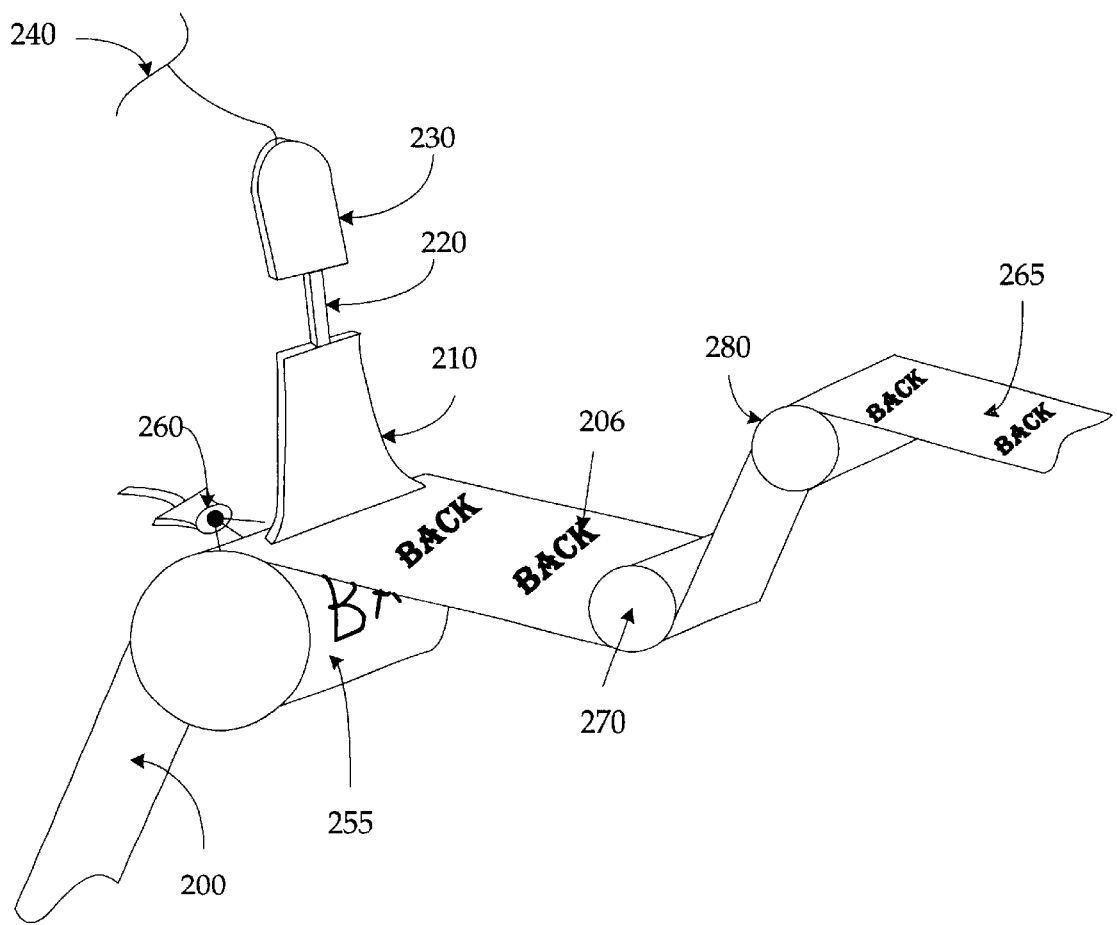
FIG. 4 is a plan view of an apparatus useful in forming an image on a moving web.

FIG. 4 is a plan view of another method and apparatus suitable for forming an image in accordance with the present invention. The ultrasonic assembly 225 in FIG. 4 is similar to the embodiment shown in FIG. 2 insofar as it is comprised of ultrasonic horn 210, booster 220, transducer 230, and controller/generator 240. Moving web 200 preferably is cooled by, inter alia, spraying cool liquid such as water via spray nozzle 260 onto the surface to ultimately be heated. The moving web 200 then passes over patterned anvil 255 which deforms web 200 in the areas where the image is to be formed (for a positive image, and in the areas where the image is not to be formed for a negative image). Patterned anvil 255 can be positioned upstream in the machine direction of ultrasonic assembly 225, (FIG. 5) or it can deform the web 200 directly underneath ultrasonic horn 210, as shown in FIG. 4.

Ultrasonic assembly 225 imparts sufficient energy to raise the surface temperature of the moving web to slightly above the melting temperature of the moving web 200 only in the areas where the image is to be formed and thereby precisely melt (partially or fully) the surface thereof and form the image. The moving web 200 now has an image 206 formed thereon to provide a printed web 265. Printed web 265 can be transported past ultrasonic assembly 225, and downstream for further processing via feed or nip rollers 270, 280, or any other mechanism known in the art.

Printed web 265 can be a back sheet layer of an absorbent article. By "back sheet," it is meant either the outermost layer of the absorbent garment or an inner layer to the extent the outer cover layer is transparent and/or translucent. Skilled artisans will recognize that the outermost layer of the absorbent article also can be comprised of a laminate of materials, of which printed web 265 is one, or that printed web 265 can be disposed on or between the outermost layer(s) and one or more inner layer(s). Printed web 265 also can be an appliqué layer that then is subsequently cut and placed in a suitable location on the absorbent article so that image 206 may be seen.

Figure 5:
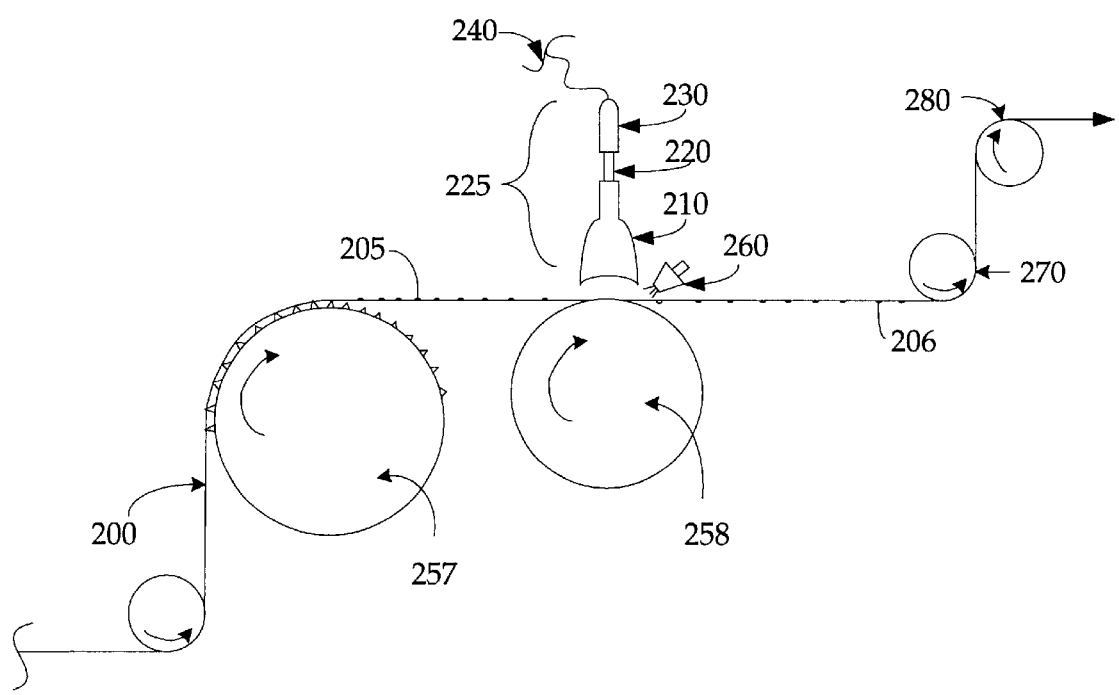
FIG. 5 is a schematic of another embodiment of an apparatus useful in forming an image on a moving web.

FIG. 5 illustrates an embodiment whereby patterned roller 257 is upstream in the machine direction from ultrasonic assembly 225. Moving web 200 passes over patterned roller 257 which forms a series of deformations (e.g., bumps 205) on the web in a pattern to form a suitable image. The web 200 having the deformations 205 then is passed between a slave anvil or cylinder 258 and ultrasonic assembly 225. The slave cylinder 258 may be made from any suitable material, including but not limited to, steel, resilient polymeric materials, resilient natural materials, and the like. Ultrasonic assembly 225 may be any ultrasonic apparatus, including the ultrasonic rotary horn 215 apparatus illustrated in FIG. 3. In addition, each of the components may be driven, may be stationary, or may be permitted to freely rotate, as described above. Again, feed or nip rollers 270, 280 may be supplied to move web 200 through the imaging apparatus.

Figure 6A:
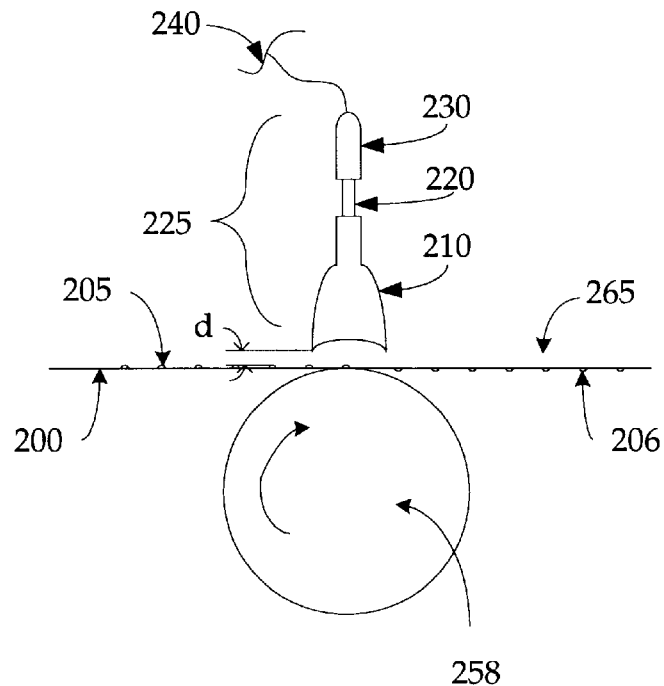
FIGS. 6a and 6b are side views of an ultrasonic horn and anvil in accordance with various features of the invention.
Figure 6B:
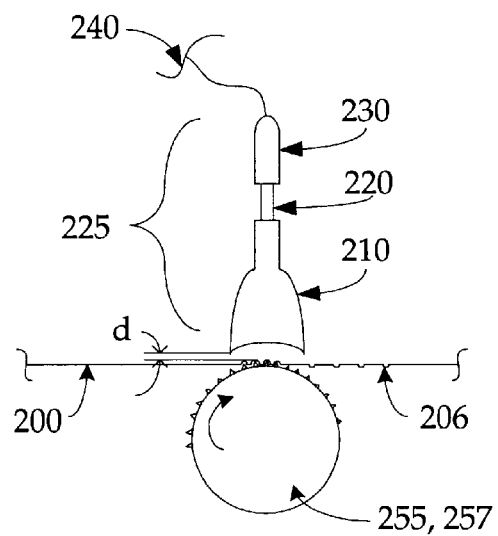

FIGS. 6a and 6b are segmented views of the imaging apparatus of the invention, including ultrasonic assembly 225 and either slave anvil 258 (FIG. 6a) or patterned anvil 255, 257 (FIG. 6b). As shown in FIG. 6a, a moving web 200 having deformations 205 thereon is transported between ultrasonic assembly 225 and slave cylinder 258. The distance between the deformations 205 and the closest ultrasonic assembly will come to the surface of moving web 200 when at rest ("d" in FIGS. 6a and 6b) can be anywhere between about 0.0001 inch to about 0.01 inch, preferably from about 0.00025 inch to about 0.0075 inch, and most preferably from about 0.0005 inch to about 0.05 inch.

Those skilled in the art will appreciate that there are various methods of deforming web 200 so that it may ultimately be imaged using any of the ultrasonic assemblies 225 described herein and known in the art or later discovered. Thus, moving web 200 may be deformed in a conventional embossing manner by raising the surface thereof to form a plurality of bumps 205. Other means of deforming web 200 may not produce bumps 205, but may produce other deformations 205 in web. For example, a suitable liquid may be sprayed on moving web 200 so that when heated by ultrasonic assembly 225, the portions contacted with the liquid melt at a temperature lower than those portions not contacted with the liquid to thereby form a positive image, or the portions contacted with liquid melt at a higher temperature to form a negative image. Various liquids include ionic liquids, water, inks, aromatic and non-aromatic solvents, and the like. The distance "d" between the closest ultrasonic assembly 225 comes to web 200 when at rest, and the apex of deformations or bumps 205 is within the above range, regardless of whether bumps 205 are formed in web 200 or not.

The method illustrated in FIG. 6b shows an alternative method of deforming web 200. Here, the web 200 is deformed directly opposite ultrasonic assembly 225 instead of upstream in the machine direction, as shown in FIG. 6a. Ultrasonic assembly 225 will impart sufficient energy to web 200 in both embodiments (FIGS. 6a and 6b) to raise the surface temperature of the moving web 200 only in the areas where the image is to be formed (e.g., only at deformations 205), to slightly above the melting temperature of the moving web 200, and thereby precisely melt the surface thereof and form the image.

Figure 7A:
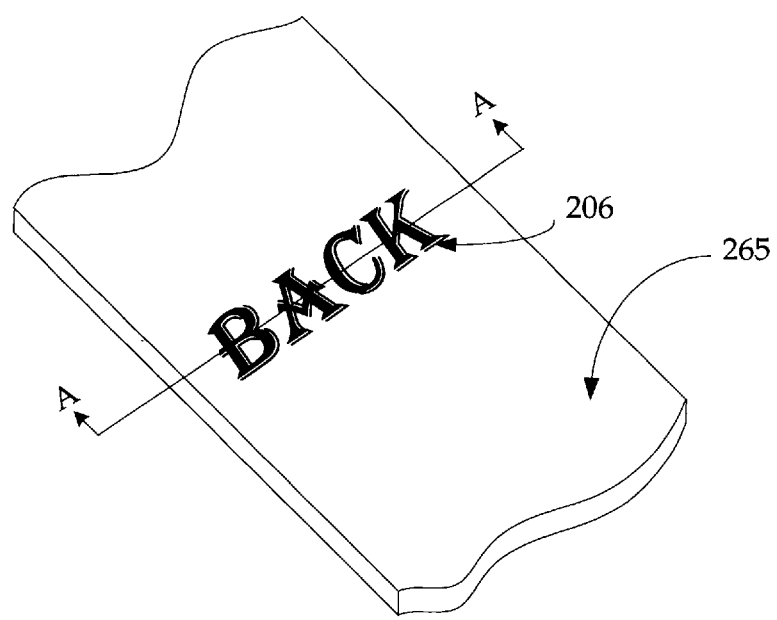
FIG. 7a is a top view of a web having an image imprinted therein in accordance with the invention.
Figure 7B:
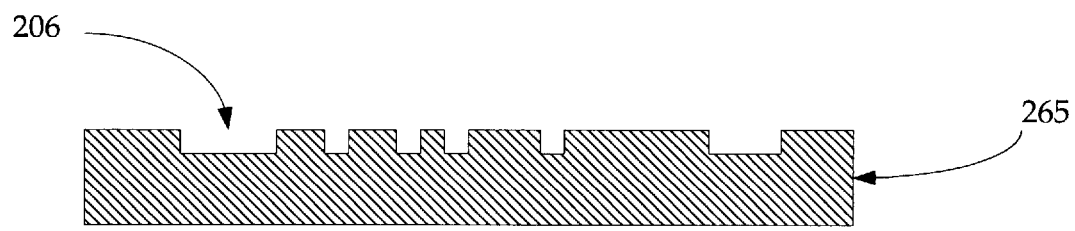
FIG. 7b is a side view of the web of FIG. 7 along line A—A.

As shown more clearly in FIGS. 7a and 7b, melting the surface of moving web 200 preferably causes slight depressions 206 to be formed to produce printed web 265. The image 206 also may be formed so that no depressions or only very slight depressions are formed in web 200. For example, the web may be stretched to a greater degree in the precise areas where ultrasonic energy melted the surface 205 of the web 200, thereby creating a different shade or degree of transparency or opaqueness in each imaged area 206. The thickness of the web 200 may be altered in the imaged areas 206, or the imaged areas may be made transparent or opaque (depending on the type of image, positive or negative, and depending on whether precisely melting causes the film to be rendered opaque or transparent). For example, all areas except those where the image is formed may be deformed, partially or fully melted by the ultrasonic apparatus 225, and then deformed due to the tension created by the moving web to render those areas transparent. The areas where the image is to be formed (which were not deformed) may remain opaque or translucent thereby revealing the image.

The invention also encompasses a method and apparatus for forming an absorbent article having an image printed thereon. The method preferably includes providing a continuously moving central absorbent pad, a continuously moving top sheet material, and a continuously moving liquid impermeable back sheet material. The method further includes forming a continuously moving absorbent core assembly at a forming station by disposing the continuously moving central absorbent pad between the continuously moving top sheet material and the continuously moving liquid impermeable back sheet material, and securing the respective components of the continuously moving absorbent core assembly together. The method also includes forming an image on the liquid impermeable back sheet material of the continuously moving absorbent core assembly by imparting sufficient ultrasonic energy with an ultrasonic horn to the back sheet layer to raise the surface temperature to slightly above the melting temperature of the back sheet layer only in the areas where the image is to be formed, thereby forming an image.

The apparatus for forming an absorbent garment having an image thereon preferably includes a mechanism for continuously supplying a top sheet material, a mechanism for continuously supplying a back sheet material, and a mechanism for continuously supplying an absorbent core. The apparatus also includes a forming station for bringing the back sheet material, top sheet material and absorbent core into engagement with one another by disposing the absorbent core between the top sheet material and the back sheet material.

The apparatus also includes a mechanism for transporting a web comprised of at least one thermoplastic material past an ultrasonic horn, and an imaging roll capable of deforming the surface of the web, whereby the deformed surface preferably corresponds to the image to be formed (if a positive image is to be formed). The apparatus further includes an ultrasonic assembly that includes an ultrasonic horn positioned relative to the moving web such that the minimum distance between the ultrasonic horn, when at rest, and the deformed surface of the web, is from about 0.0001 to about 0.01 inch. The apparatus further includes a mechanism for controlling the amount of energy ultimately imparted to the ultrasonic horn such that the horn provides sufficient ultrasonic energy to the moving web to raise the surface temperature of the deformed surfaces to slightly above the melting temperature of the web. In one embodiment, the web is the back sheet material, and the ultrasonic horn is disposed in the machine direction either prior to, or after the forming station. In another embodiment, the web is an appliqué layer, the ultrasonic horn is disposed in a position independent from the forming station, and the apparatus further includes a mechanism for cutting and disposing the appliqué layer containing the image on the back sheet material either prior to, or after the back sheet material travels through the forming station.

A particularly preferred method and apparatus suitable for forming an absorbent article having an image thereon will be described hereinafter with reference to FIG. 8. The absorbent article generally is formed at forming station 800 where top sheet material 24, back sheet material 26, absorbent core 28 and elastic elements 30 are brought together to form an article. Additional layers may be added upstream or downstream in a machine direction from forming station 800, including an outer non-woven having an appliqué layer containing an image disposed thereon.

The image can be an image prepared in accordance with the procedures and apparatus described above, or it can be a separate graphics material denoting any suitable character or object graphic together with an image prepared in accordance with the inventive process.

Figure 8:
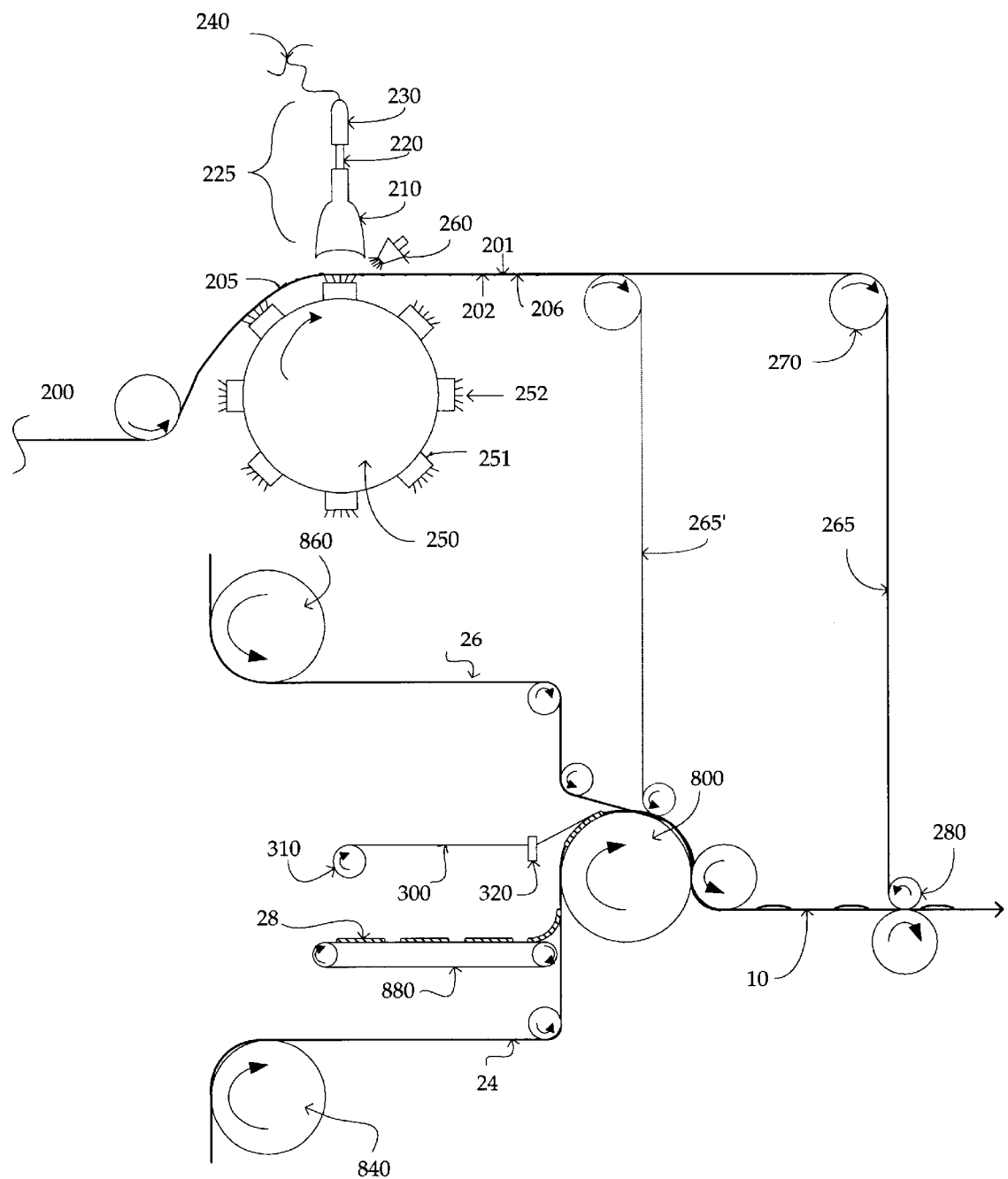
FIG. 8 is a schematic of an apparatus useful in forming an absorbent article having an image thereon, whereby the absorbent article is made in accordance with the invention.

The back sheet material 26 may have an image formed thereon in accordance with the invention, as shown in FIG. 8, or any image may be formed on the overall article in accordance with the invention downstream in the machine direction from forming station 800. For example, back sheet material 26 may be replaced by printed web 265' in FIG. 8, as indicated by the dotted rollers and the dotted line. In this optional embodiment of the invention, feed roller 860 would not be needed, and printed web 265 would be fed to forming station 800.

On-line forming of an image on back sheet material 26 may be accomplished in accordance with the present invention by passing moving web 200 through an imaging station that generally includes an ultrasonic assembly 225, web 200, and a mechanism for deforming web 200. The mechanism for deforming web 200 may include a patterned anvil 250 (or 255), a patterned roller 257, a pin roller (not shown), or an applicator that sprays an ingredient on web 200 in the image areas (for a positive image or non-image areas for a negative image) to deform that portion of web so that it melts at a temperature lower than other portions of the web 200 that were not treated. It is preferred that web 200 be cooled with a cooling apparatus 260 prior to passing through the imaging station.

In FIG. 8, the mechanism for deforming web 200 includes a patterned anvil 250 that includes projections 251 with raised elements 252 deforming the underside of web 202. The deformed web containing deformations 205 then is (or simultaneously is) imparted with sufficient ultrasonic energy to precisely melt the surface of web 200 at the deformations 205 to thereby form an image 206. Any ultrasonic assembly 225 can be used to impart the energy. FIG. 8 illustrates a preferred assembly including an ultrasonic horn 210 (which also may be an ultrasonic rotary horn 215, see FIG. 3), booster 220, transducer 230, and generator/controller 240, which serves to control the frequency and strength of reciprocating vibrations in ultrasonic horn 210. The energy generated by ultrasonic assembly 225 is sufficient to form image 206 on now printed web 265. Printed web then can be transported to forming station 800 via pinch rollers, feed rollers, and/or nip rollers 270, 280. If the printed web 265 is prepared in-line with the absorbent article 10, then it can be fed directly to forming station in lieu of back sheet supply roller 860. If printed web 265 is prepared off line, a roll of printed web material 265 can be supplied to forming station 800 via rollers 270, 280. In the embodiment shown in FIG. 8, printed web 265 is the back sheet 26 of the absorbent article.

An alternative embodiment of the invention (not shown in FIG. 8) includes first forming at forming station 800 an absorbent material that includes a top sheet material 24, a back sheet material 26, and an absorbent core 28 and elastic elements 30 disposed there between. The absorbent material then can be fed to the imaging station as moving web 200, and the back sheet material 26 imaged in accordance with the present invention. In this embodiment, ultrasonic assembly 225 would be disposed downstream of forming station 800.

A top sheet supply roller 840 can continuously supply top sheet material 24 to forming station 800. It is preferred that absorbent core 28 be adhered to top sheet material 24 (or back sheet 26 or printed web 265) prior to forming station 800, as shown in FIG. 8. Here, absorbent core 28 is transported via conveyor 880 and adhered to top sheet material 24 prior to forming station 800. As described above with reference to FIG. 1, it is preferred that the absorbent article include a variety of additional elements, including leg gathers 30 that are created by incorporation of elastic elements 300. Elastic elements 300 can be continuously supplied to forming station 800 via elastic supply roller 310, and elastic supply applicator 320. If adhesives are used to adhere any of the respective components to one another, the adhesives typically are applied upstream in the machine direction from forming station 800. The adhesives can be applied directly to the components, or adhesives may be applied to top sheet 24, back sheet 26, and/or printed web 265 in various patterns using techniques known in the art. The respective components, including top sheet material 24, back sheet 26 (or printed web 265), elastic elements 300, and absorbent core 28, all are fed to forming station 800 where they are brought into contact with one another and formed into absorbent article 10.

As mentioned above, a variety of other layers and/or elements and/or components may be included in absorbent article 10. These layers, elements, and/or components may be disposed on the components discussed above (or disposed on the formed article 10) either prior to, or after forming station 800. For example, an additional appliqué layer(s) containing multicolored graphics can be added to an outer non-woven material that then is associated with back sheet 26 (or printed web 265). An image 206 may be formed directly on back sheet 26 after formation of absorbent article 10 in forming station 800 using the methods and apparatus described herein with reference to FIGS. 2–7. This image may be in addition to an image already formed on printed web 265, and/or in addition to an image formed on an appliqué layer that then is disposed on back sheet 26 (or printed web 265).

The present invention provides absorbent articles having images and graphics accurately positioned with respect to other components of the absorbent article. Examples of graphics include, but are not limited to, characters; objects; lines and other segmentation indicia; indicia highlighting or emphasizing leg and waist openings in order to make product shaping more evident or visible to the user; indicia highlighting or emphasizing areas of the product to simulate functional components such as elastic leg bands, elastic waistbands, and fly openings; indicia highlighting areas of the product to change the appearance of the size of the product; wetness indicators, temperature indicators, fit indicators, and the like; front and/or back labels or pictorials; or written instructions.

As mentioned above, the resulting absorbent article can preferably include two images or graphics thereon—one on the front waist panel and another on the rear waist panel. The graphics on the front and rear waist panels preferably aesthetically correspond to each other, although they need not aesthetically correspond or otherwise relate to one another. The term "aesthetically correspond" means that the graphics pictorially interrelate to one another. For instance, the graphics can depict a scene from both the front perspective and the rear perspective.

The invention has been described in connection with the above preferred embodiments. These embodiments, however, are merely illustrative and the invention is not restricted thereto. It will be understood by those skilled in the art that other variations and modifications can easily be made within the scope of the invention as defined by the appended claims.

What is claimed is:

1. A method of forming an image on a moving non-woven web comprising
    feeding a moving non-woven web past an ultrasonic assembly;
    imparting sufficient ultrasonic energy to the moving web with the ultrasonic assembly to raise the surface temperature of the moving web to slightly above the melting temperature of the moving web only in the areas where the image is to be formed for a positive image, or only in the areas where the image is not to be formed for a negative image, to thereby form the image,
    whereby imparting sufficient ultrasonic energy includes vibrating the ultrasonic assembly transversely to the direction of the moving web such that the ultrasonic assembly only briefly comes into contact with the moving web that is imaged when the horn is fully extended, and the amount of energy imparted by the ultrasonic assembly is controlled to prevent forming a hole in the moving web.

2. The method of claim 1, wherein the moving non-woven web forms a part of an absorbent article.

3. The method of claim 1, wherein the moving web is an appliqué layer that is adhered to or otherwise associated with an absorbent article.

4. The method of claim 1, wherein the ultrasonic assembly comprises a transducer, a booster, and an ultrasonic horn operatively associated with one another, whereby the ultrasonic horn vibrates transversely to the direction of the moving web.

5. The method of claim 1, wherein the moving non-woven web is comprised of one or more materials selected from the group consisting of: a spun-bonded non-woven web of synthetic fibers selected from polypropylene, polyethylene, and polyester fibers, and mixtures thereof; a non-woven web of cellulosic fibers, textile fibers selected from rayon fibers or cotton fibers, or a blend of cellulosic and textile fibers; a spun-bonded non-woven web of synthetic fibers selected form polypropylene; polyethylene, and polyester fibers, mixed with cellulosic, pulp fibers, or textile fibers; and melt blown thermoplastic fibers selected from macro fibers or micro fibers of polypropylene, polyethylene, polyester or other thermoplastic materials, or mixtures of such thermoplastic macro fibers or micro fibers with cellulosic, pulp or textile fibers.

6. The method of claim 5, wherein the moving non-woven web is a spun-bonded non-woven web of polypropylene.

7. The method of claim 1 wherein power is supplied to the ultrasonic assembly by a variable power supply at a rate of about 1,000 amp.

8. The method of claim 1, wherein the ultrasonic assembly vibrates at a frequency within the range of from about 20 kHz to about 40 kHz.

9. The method of claim 1, wherein the ultrasonic assembly vibrates at an amplitude within the range of from about 10 to about 120 μm.

10. The method of claim 1, wherein the ultrasonic assembly comprises a booster that boosts the power supplied to the ultrasonic assembly at a ratio within the range of from about 0.6:1 to about 2.5:1.

11. The method of claim 1, wherein the ultrasonic assembly comprises an ultrasonic horn that is comprised of a material selected from aluminum, titanium, and mixtures thereof.

12. The method of claim 1, wherein the image is a colored image formed by disposing underneath the moving non-woven web a colored material, whereby the imaged areas present on the non-woven web material are sufficiently translucent to reveal the colored material disposed thereunder.

13. The method of claim 1, wherein the non-woven web is transported past the ultrasonic assembly at a speed within the range of from about 50 to about 500 feet/min.

14. A method of forming an absorbent article comprising:
   providing a top sheet material;
   providing an absorbent core;
   forming an image on a moving liquid impermeable back sheet material by:
      imparting sufficient ultrasonic energy with an ultrasonic assembly to the back sheet material to raise the surface temperature only in the areas where the image is to be formed to slightly above the melting temperature of the back sheet material to thereby form a liquid impermeable imaged back sheet material;
   providing a continuously moving liquid impermeable imaged back sheet material; and
   forming an absorbent article by disposing the absorbent core between the continuously moving top sheet material and the continuously moving liquid impermeable imaged back sheet material.

15. The method of claim 14, further comprising disposing at least one additional layer between the absorbent core and the top sheet material.

16. The method of claim 15, wherein the at least one additional layer is selected from the group consisting of a fluid acquisition layer, a distribution layer, an additional absorbent core optionally containing superabsorbent polymer, a wicking layer, a storage layer, and combinations and fragments thereof.

17. The method of claim 14, wherein the ultrasonic assembly comprises a transducer, a booster, and an ultrasonic horn operatively associated with one another, whereby the ultrasonic horn vibrates transversely to the direction of the moving liquid impermeable back sheet material.

18. The method of claim 14 wherein power is supplied to the ultrasonic assembly by a variable power supply at a rate of about 1,000 amp.

19. The method of claim 14, wherein the ultrasonic assembly vibrates at a frequency within the range of from about 20 kHz to about 40 kHz.

20. The method of claim 14, wherein the ultrasonic assembly vibrates at an amplitude within the range of from about 10 to about 120 $\mu$m.

21. The method of claim 14, wherein the ultrasonic assembly comprises a booster that boosts the power supplied to the ultrasonic assembly at a ratio within the range of from about 0.6:1 to about 2.5:1.

22. The method of claim 14, wherein the ultrasonic assembly comprises an ultrasonic horn that is comprised of a material selected from aluminum, titanium, and mixtures thereof.

23. The method of claim 14, wherein the image is a colored image formed by disposing underneath the moving liquid impermeable back sheet material a colored material, whereby the imaged areas present on the back sheet material are sufficiently translucent to reveal the colored material disposed thereunder.

24. The method of claim 14, wherein the moving liquid impermeable back sheet material is transported past the ultrasonic assembly at a speed within the range of from about 50 to about 500 feet/min.

25. A method of making an absorbent article comprising:
   providing a top sheet material;
   providing an absorbent core;
   providing a liquid impermeable back sheet material;
   fornming an image on a moving appliqué layer by
      imparting sufficient ultrasonic energy with an ultrasonic assembly to the appliqué layer to raise the surface temperature only in the areas where the image is to be formed to slightly above the melting temperature of the appliqué layer to form an imaged appliqué layer;
   forming a continuously moving absorbent core assembly at a forming station by disposing the absorbent core between the top sheet material and the liquid impermeable back sheet material;
   providing a continuously moving imaged appliqué layer; and
   disposing the continuously moving imaged appliqué layer on a surface of the continuously moving absorbent core assembly.

26. The method of claim 25, further comprising disposing at least one additional layer between the absorbent core and the top sheet material.

27. The method of claim 26, wherein the at least one additional layer is selected from the group consisting of a fluid acquisition layer, a distribution layer, an additional absorbent core optionally containing superabsorbent polymer, a wicking layer, a storage layer, and combinations and fragments thereof.

28. The method of claim 25, wherein the ultrasonic assembly comprises a transducer, a booster, and an ultrasonic horn operatively associated with one another, whereby the ultrasonic horn vibrates transversely to the direction of the moving appliqué layer.

29. The method of claim 25, wherein power is supplied to the ultrasonic assembly by a variable power supply at a rate of about 1,000 amp.

30. The method of claim 25, wherein the ultrasonic assembly vibrates at a frequency within the range of from about 20 kHz to about 40 kHz.

31. The method of claim 25, wherein the ultrasonic assembly vibrates at an amplitude within the range of from about 10 to about 120 $\mu$m.

32. The method of claim 25, wherein the ultrasonic assembly comprises a booster that boosts the power supplied to the ultrasonic assembly at a ratio within the range of from about 0.6:1 to about 2.5:1.

33. The method of claim 25, wherein the ultrasonic assembly comprises an ultrasonic horn that is comprised of a material selected from aluminum, titanium, and mixtures thereof.

34. The method of claim 25, wherein the image is a colored image formed by disposing underneath the moving imaged appliqué layer a colored material, whereby the imaged areas present on the imaged appliqué layer are sufficiently translucent to reveal the colored material disposed there under.

35. The method of claim 25, wherein the appliqué layer is transported past the ultrasonic assembly at a speed within the range of from about 50 to about 500 feet/min.

36. The method of claim 25, wherein the appliqué layer is comprised of one or more materials selected from the group consisting of: a spun-bonded non-woven web of synthetic fibers selected from polypropylene, polyethylene, and polyester fibers, and mixtures thereof; a non-woven web of cellulosic fibers, textile fibers selected from rayon fibers or cotton fibers, or a blend of cellulosic and textile fibers; a spun-bonded non-woven web of synthetic fibers selected form polypropylene; polyethylene, and polyester fibers, mixed with cellulosic, pulp fibers, or textile fibers; and melt blown thermoplastic fibers selected from macro fibers or micro fibers of polypropylene, polyethylene, polyester or other thermoplastic materials, or mixtures of such thermoplastic macro fibers or micro fibers with cellulosic, pulp or textile fibers.

37. The method of claim 36, wherein the moving non-woven web is a spun-bonded non-woven web of polypropylene.

38. A method of imparting an image to an absorbent article comprising:

providing an absorbent core;

providing a top sheet material;

providing a liquid impermeable back sheet material;

forming a continuously moving absorbent core assembly having at least one outer surface at a forming station by disposing the absorbent core between the top sheet material and the back sheet material; and forming an image on the continuously moving absorbent core assembly by imparting sufficient ultrasonic energy with an ultrasonic assembly to the at least one outer layer to raise the surface temperature thereof only in the areas where the image is to be formed to slightly above the melting temperature of the outer layer.

39. The method of claim 38, wherein the ultrasonic assembly comprises a transducer, a booster, and an ultrasonic horn operatively associated with one another, whereby the ultrasonic horn vibrates transversely to the direction of the moving web.

40. The method of claim 38, wherein power is supplied to the ultrasonic assembly by a variable power supply at a rate of about 1,000 amp.

41. The method of claim 38, wherein the ultrasonic assembly vibrates at a frequency within the range of from about 20 kHz to about 40 kHz.

42. The method of claim 38, wherein the ultrasonic assembly vibrates at an amplitude within the range of from about 10 to about 120 µm.

43. The method of claim 38, wherein the ultrasonic assembly comprises a booster that boosts the power supplied to the ultrasonic assembly at a ratio within the range of from about 0.6:1 to about 2.5:1.

44. The method of claim 38, wherein the ultrasonic assembly comprises an ultrasonic horn that is comprised of a material selected from aluminum, titanium, and mixtures thereof.

45. The method of claim 38, wherein the image is a colored image formed by disposing underneath the at least one outer layer a colored material, whereby the imaged areas present on the at least one outer layer are sufficiently translucent to reveal the colored material disposed thereunder.

46. The method of claim 38, wherein the continuously moving absorbent core assembly is transported past the ultrasonic assembly at a speed within the range of from about 50 to about 500 feet/min.

47. An apparatus for imparting an image to a moving web comprising:

a mechanism for transporting the web in a machine direction and past an ultrasonic assembly;

an imaging roll capable of deforming the surface of the web without punching holes there through, whereby the deformed surface corresponds to either a positive or a negative of the image to be formed;

an ultrasonic assembly positioned relative to the moving web such that the minimum distance between the ultrasonic assembly at rest and the deformed surface of the web is from about 0.0005 to about 0.005 inch; and a mechanism for controlling the amount of energy imparted to the ultrasonic assembly such that the ultrasonic assembly provides sufficient ultrasonic energy to the moving web to raise the surface temperature of the deformed surfaces to slightly above the melting temperature of the web only in the areas where the image is to be formed.

48. The apparatus of claim 47, wherein the mechanism for providing the web is a feed roller.

49. The apparatus of claim 47, wherein the imaging roll is disposed opposite the ultrasonic assembly from the moving web.

50. The apparatus of claim 47, wherein the imaging roll is disposed upstream in the machine direction from the ultrasonic assembly.

51. The apparatus of claim 47, wherein the ultrasonic assembly comprises a rotary ultrasonic horn.

52. The apparatus of claim 47, wherein the ultrasonic assembly comprises a transducer, a booster, and an ultrasonic horn operatively associated with one another, whereby the ultrasonic horn vibrates transversely to the direction of the moving web.

53. The apparatus of claim 47, wherein power is supplied to the ultrasonic assembly by a variable power supply at a rate of about 1,000 amp.

54. The apparatus of claim 47, wherein the ultrasonic assembly vibrates at a frequency within the range of from about 20 kHz to about 40 kHz.

55. The apparatus of claim 47, wherein the ultrasonic assembly vibrates at an amplitude within the range of from about 10 to about 120 µm.

56. The apparatus of claim 47, wherein the ultrasonic assembly comprises a booster that boosts the power supplied to the ultrasonic assembly at a ratio within the range of from about 0.6:1 to about 2.5:1.

57. The apparatus of claim 47, wherein the ultrasonic assembly comprises an ultrasonic horn that is comprised of a material selected from aluminum, titanium, and mixtures thereof.

58. The apparatus of claim 47, wherein the moving web is transported past the ultrasonic assembly at a speed within the range of from about 50 to about 500 feet/min.

59. An apparatus for forming an absorbent garment having an image thereon comprising:

a mechanism for continuously supplying top sheet material;

a mechanism for continuously supplying back sheet material;

a mechanism for continuously supplying an absorbent core;

a forming station for bringing the back sheet material, top sheet material and absorbent core into engagement with one another by disposing the absorbent core between the top sheet material and the back sheet material;

a mechanism for transporting a web past an ultrasonic assembly;

an imaging roll capable of deforming the surface of the web without punching holes there through, whereby the deformed surface corresponds to either a positive or a negative of the image to be formed;

an ultrasonic assembly positioned relative to the moving web such that the minimum distance between the ultrasonic assembly at rest and the deformed surface of the web is from about 0.0005 to about 0.005 inch; and a mechanism for controlling the amount of energy imparted to the ultrasonic assembly such that the ultrasonic assembly provides sufficient ultrasonic energy to the moving web to raise the surface temperature of the deformed surfaces to slightly above the melting temperature of the web only in the areas where the image is to be formed.

60. The apparatus of claim 59, wherein the moving web is the back sheet material, and the ultrasonic assembly is disposed in the machine direction upstream from the forming station.

61. The apparatus of claim 59, wherein the moving web is the back sheet material, and the ultrasonic assembly is disposed in the machine direction downstream from the forming station.

62. The apparatus of claim 59, wherein the moving web is an appliqué layer, and the ultrasonic assembly is disposed in a position independent from the forming station.

63. The apparatus of claim 62, further comprising a mechanism for cutting the appliqué layer containing the image, and a mechanism for disposing the appliqué layer containing the image on the back sheet material prior to the forming station.

64. The apparatus of claim 62, further comprising a mechanism for cutting the appliqué layer containing the image, and a mechanism for disposing the appliqué layer containing the image on the back sheet material after the forming station.

65. The apparatus of claim 59, wherein the imaging roll is disposed opposite the ultrasonic assembly from the moving web.

66. The apparatus of claim 59, wherein the imaging roll is disposed upstream in the machine direction from the ultrasonic assembly.

67. The apparatus of claim 59, wherein the ultrasonic assembly comprises a rotary ultrasonic horn.

68. The apparatus of claim 59, wherein the ultrasonic assembly comprises a transducer, a booster, and an ultrasonic horn operatively associated with one another, whereby the ultrasonic horn vibrates transversely to the direction of the moving web.

69. The apparatus of claim 59, wherein power is supplied to the ultrasonic assembly by a variable power supply at a rate of about 1,000 amp.

70. The apparatus of claim 59, wherein the ultrasonic assembly vibrates at a frequency within the range of from about 20 kHz to about 40 kHz.

71. The apparatus of claim 59, wherein the ultrasonic assembly vibrates at an amplitude within the range of from about 10 to about 120 $\mu$m.

72. The apparatus of claim 59, wherein the ultrasonic assembly comprises a booster that boosts the power supplied to the ultrasonic assembly at a ratio within the range of from about 0.6:1 to about 2.5:1.

73. The apparatus of claim 59, wherein the ultrasonic assembly comprises an ultrasonic horn that is comprised of a material selected from aluminum, titanium, and mixtures thereof.

74. The apparatus of claim 59, wherein the moving web is transported past the ultrasonic assembly at a speed within the range of from about 50 to about 500 feet/min.

* * * * *